(12) United States Patent
Madhavan

(10) Patent No.: US 12,111,308 B2
(45) Date of Patent: Oct. 8, 2024

(54) BIOMARKER PLATFORM FOR PARKINSON'S DISEASE USING PATIENT-DERIVED PRIMARY DERMAL FIBROBLASTS

(71) Applicant: ARIZONA BOARD OF REGENTS ON BEHALF OF THE UNIVERSITY OF ARIZONA, Tucson, AZ (US)

(72) Inventor: Lalitha Madhavan, Tucson, AZ (US)

(73) Assignee: ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 398 days.

(21) Appl. No.: 17/147,022

(22) Filed: Jan. 12, 2021

(65) Prior Publication Data
US 2021/0132046 A1    May 6, 2021

Related U.S. Application Data

(63) Continuation of application No. 16/162,242, filed on Oct. 16, 2018, now Pat. No. 11,099,173.

(60) Provisional application No. 62/572,933, filed on Oct. 16, 2017.

(51) Int. Cl.
*G01N 33/50*     (2006.01)
*C12N 5/071*     (2010.01)

(52) U.S. Cl.
CPC ....... *G01N 33/5091* (2013.01); *C12N 5/0625* (2013.01); *G01N 33/5044* (2013.01); *G01N 2800/2835* (2013.01); *G01N 2800/52* (2013.01); *G01N 2800/60* (2013.01); *G01N 2800/7009* (2013.01)

(58) Field of Classification Search
CPC ........... G01N 33/5091; G01N 33/5044; G01N 2800/2835; G01N 2800/52; G01N 2800/60
See application file for complete search history.

(56) References Cited

PUBLICATIONS

Teves et al. Parkinson's Disease Skin Fibroblasts Display Signature Alterations in Growth, Redox Homeostasis, Mitochondrial Function, and Autophagy. Frontiers in Neuroscience. Jan. 2018, vol. 11, Article 737, pp. 1-15.
Teves et al. 42.30 / L6—Modeling Parkinson's disease using patient-derived primary dermal fibroblasts. Session 042—Parkinson's Disease: Molecular Mechanisms and Models. Poster presentation at Neuroscience 2016 on Nov. 12, 2016. Abstract.
Auburger et al., Mol. Neurobiol., 2012, 46:20-27.
Arduino et al., 2012, Human Mol. Genetics, 21 (21):4680-702.

*Primary Examiner* — Olga N Chernyshev
(74) *Attorney, Agent, or Firm* — NGUYEN TARBET IP LAW

(57) ABSTRACT

Primary skin fibroblasts obtained from individuals diagnosed with late-onset sporadic Parkinson's disease (PD), were compared to healthy age-matched controls. Fibroblasts from PD subjects had higher growth rates, and appeared distinctly different in terms of morphology and spatial organization in culture, compared to control cells. The PD fibroblasts also exhibited significantly compromised mitochondrial structure and function when assessed via morphological and oxidative phosphorylation assays. Additionally, an increase in baseline macroautophagy levels was seen in cells from PD subjects. Exposure of the skin fibroblasts to physiologically relevant stress, specifically ultraviolet irradiation (UVA), further exaggerated the autophagic dysfunction in the PD cells. Moreover, the PD fibroblasts accumulated higher levels of reactive oxygen species (ROS) coupled with lower cell viability upon UVA treatment. These results highlight primary skin fibroblasts as a patient-relevant model that captures fundamental PD molecular mechanisms, and enable their utility as diagnostic and prognostic biomarkers for PD.

6 Claims, 25 Drawing Sheets
(15 of 25 Drawing Sheet(s) Filed in Color)

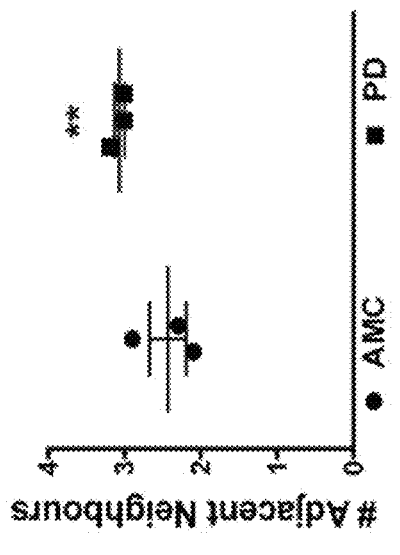
FIG. 2L
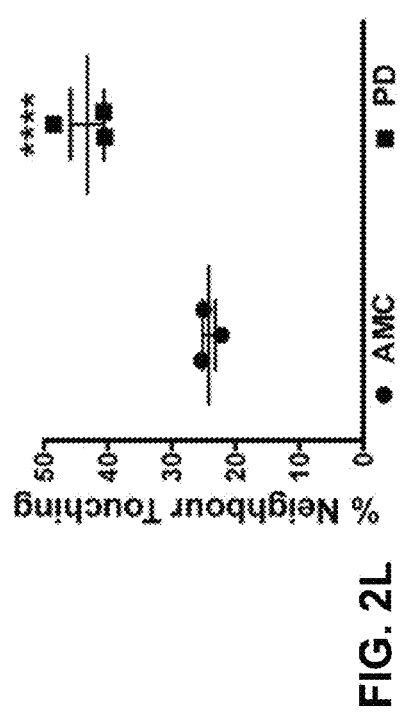
FIG. 2M
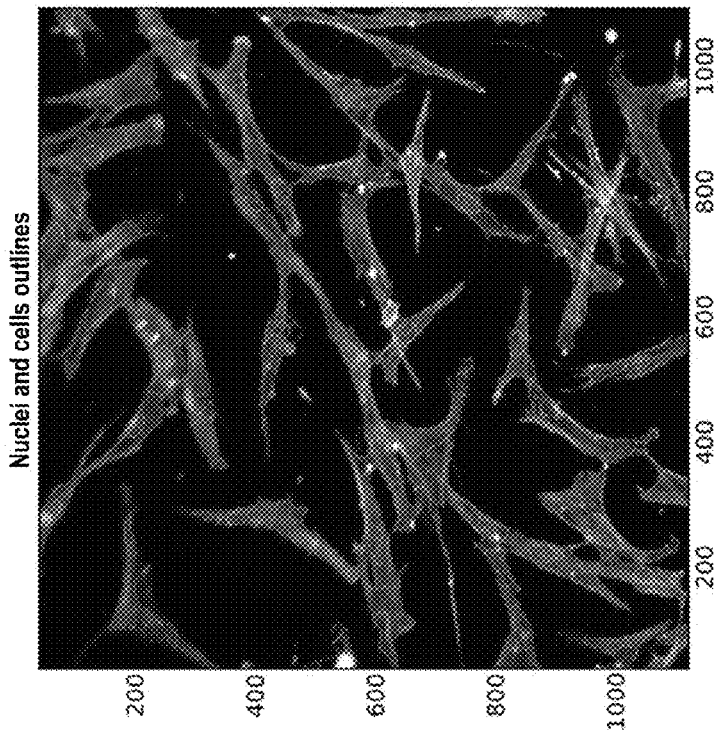
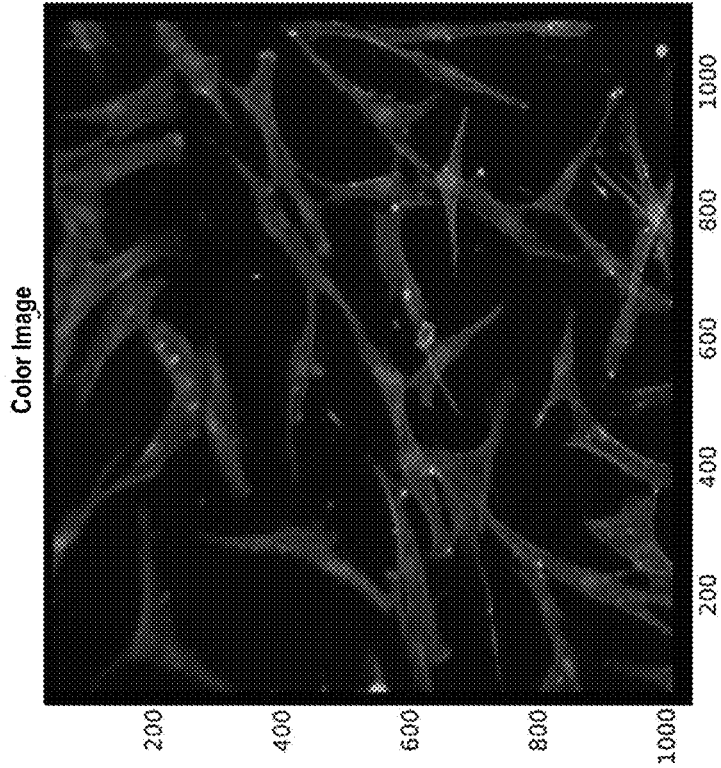
FIG. 3A

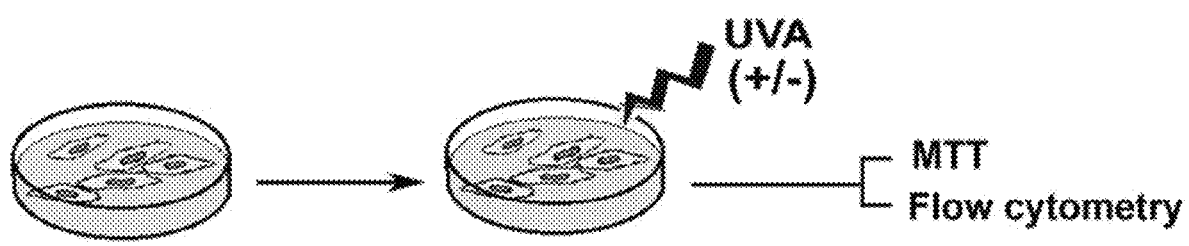
FIG. 4A
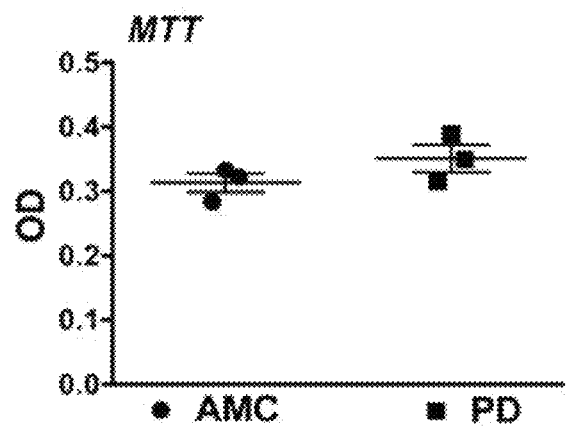
FIG. 4B
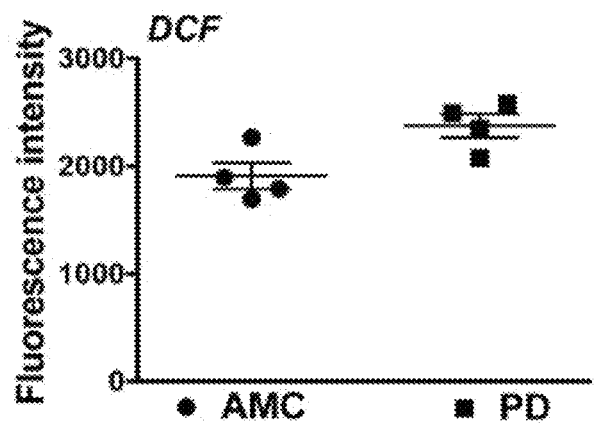
FIG. 4C
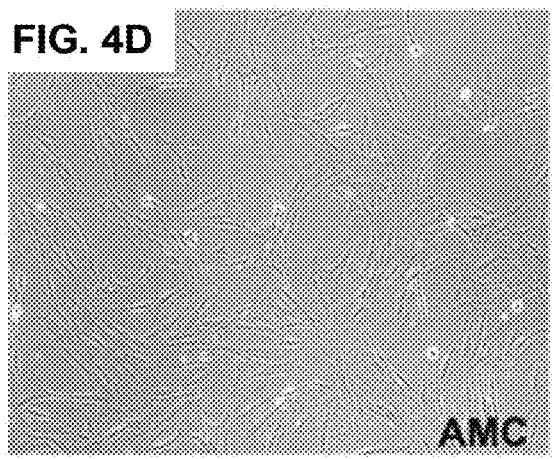
FIG. 4D AMC
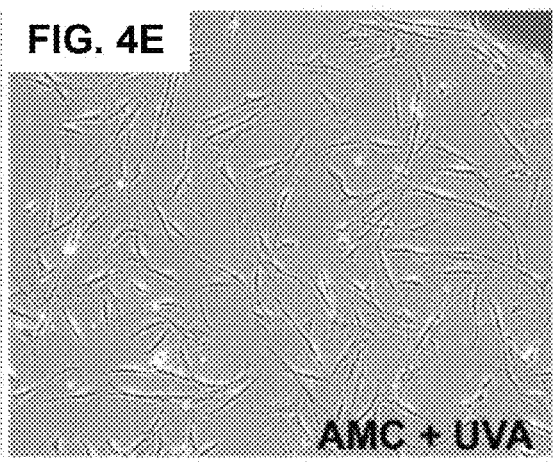
FIG. 4E AMC + UVA
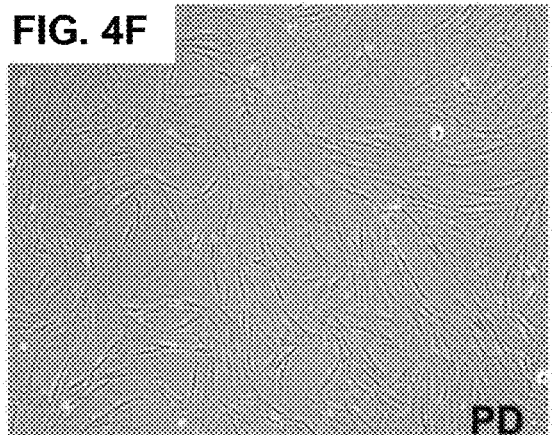
FIG. 4F PD
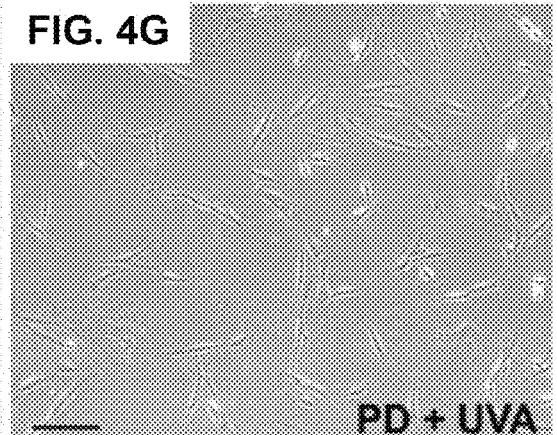
FIG. 4G PD + UVA

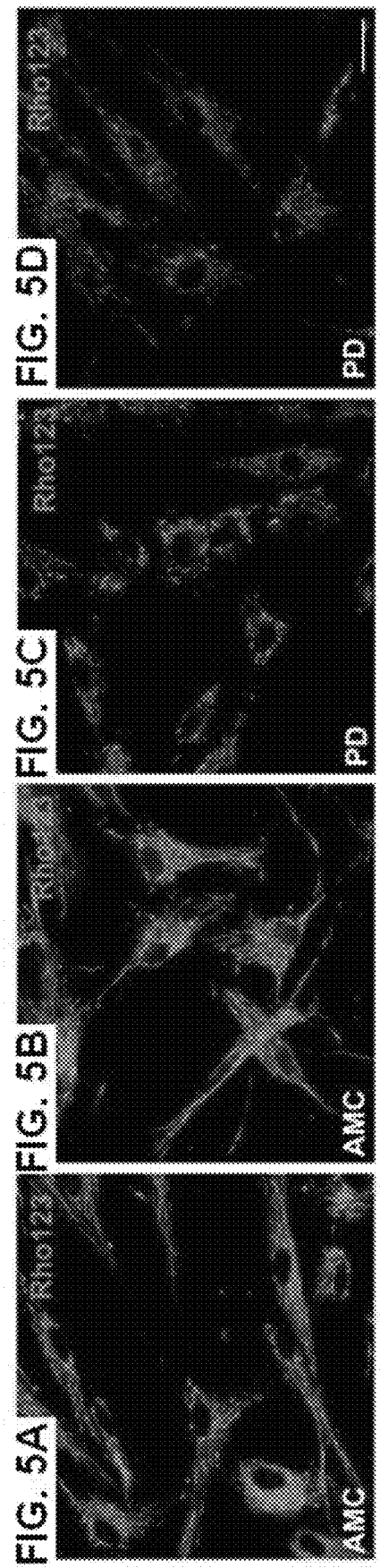
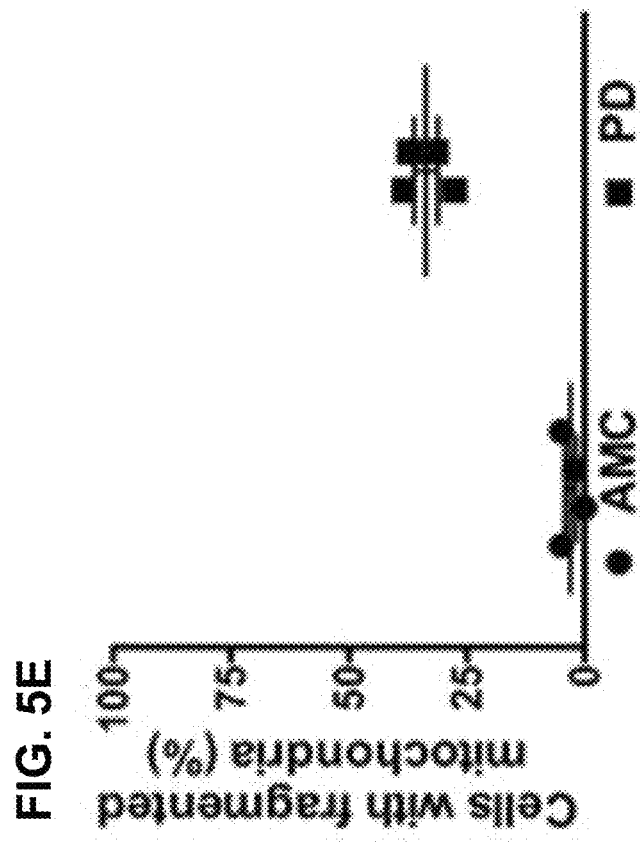

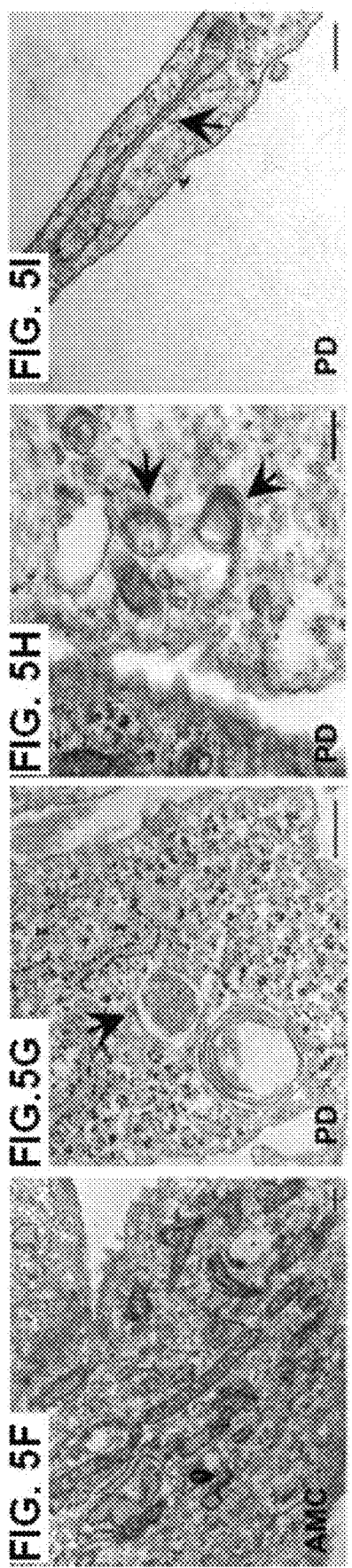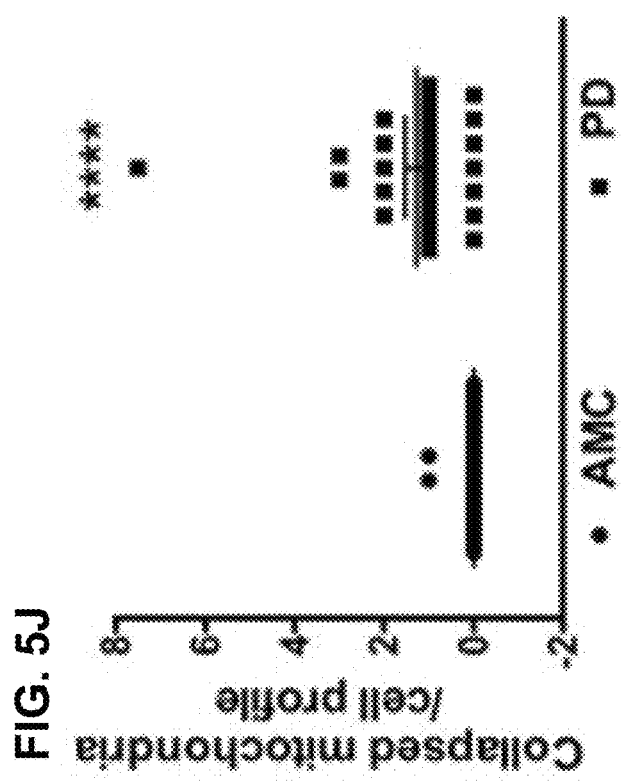

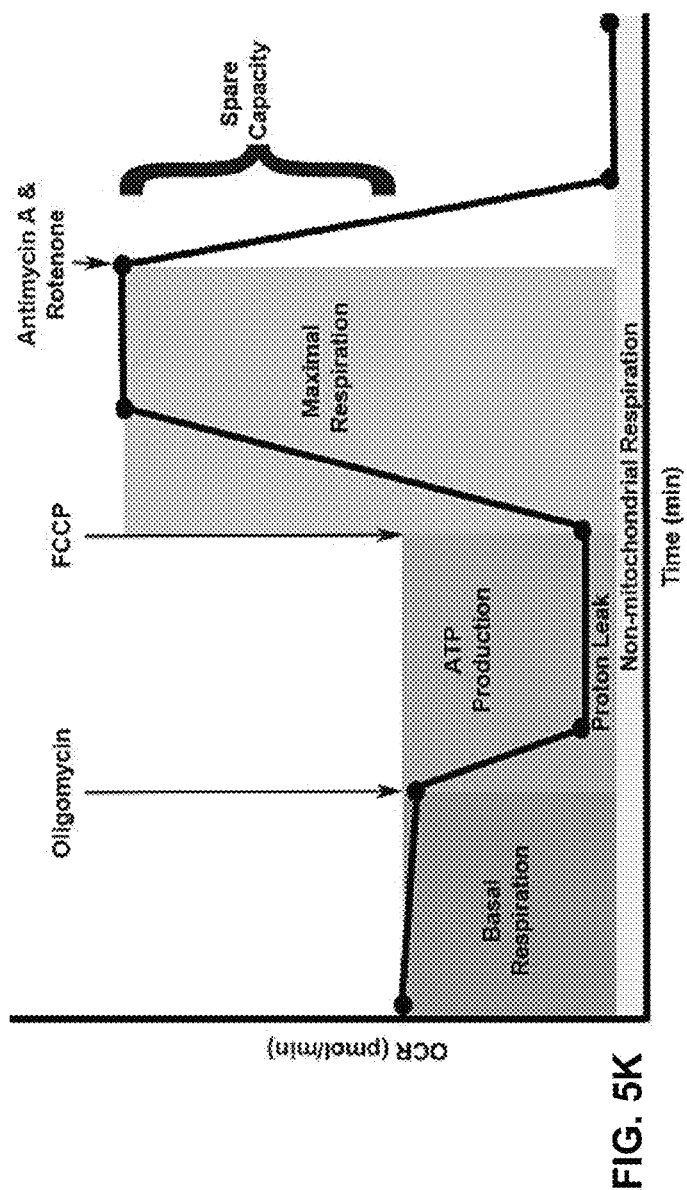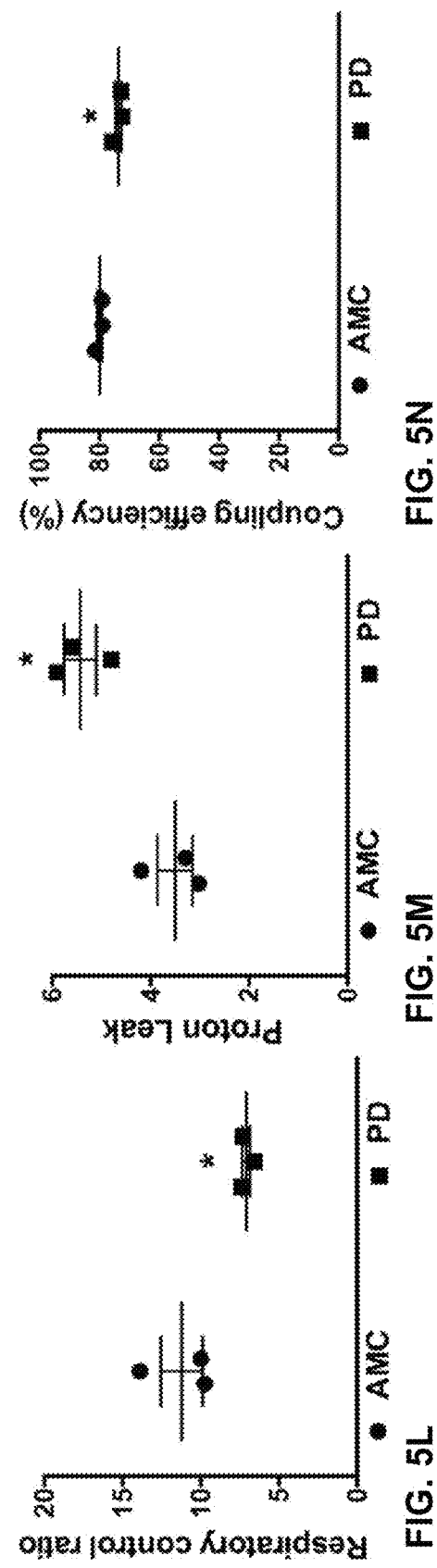
FIG. 5K  FIG. 5L  FIG. 5M  FIG. 5N

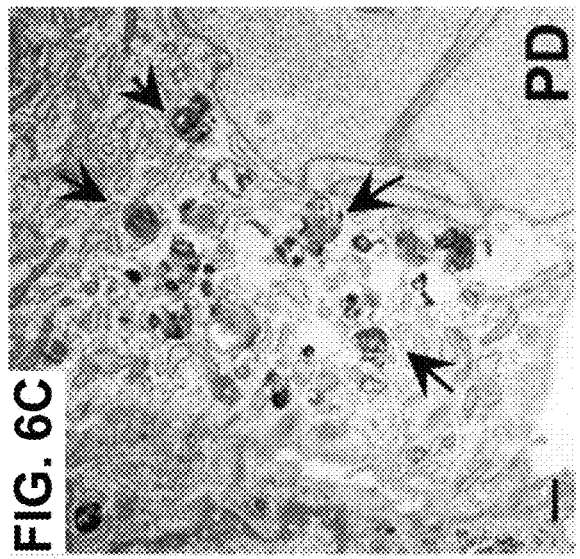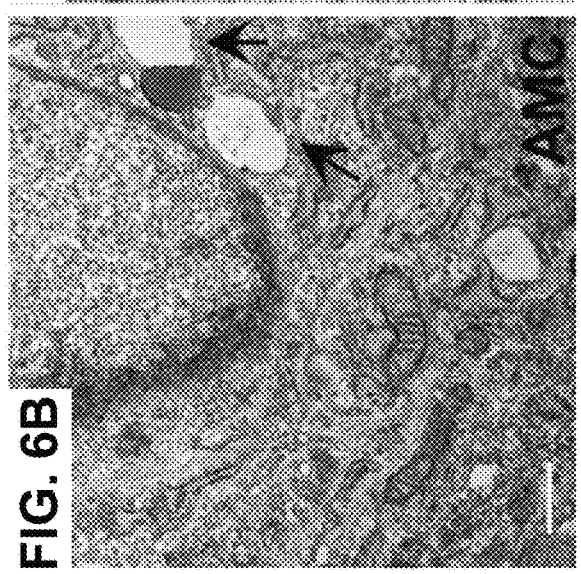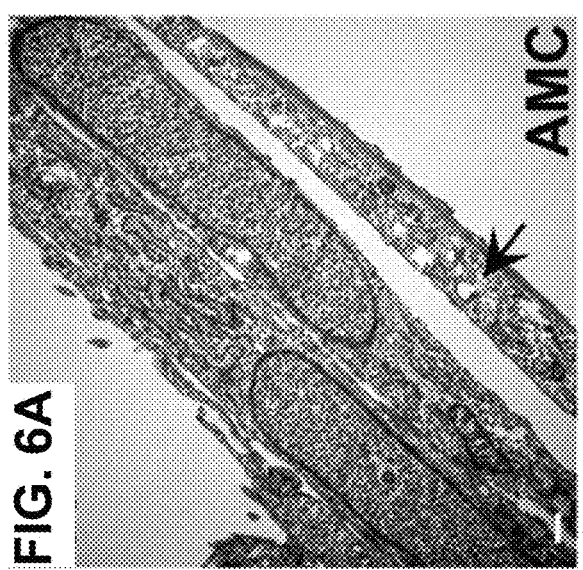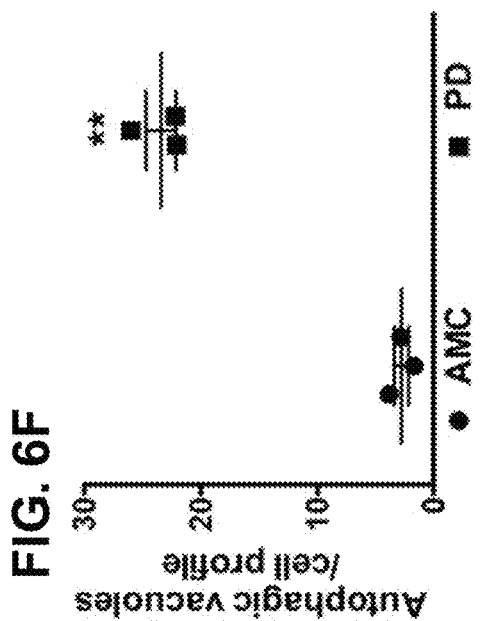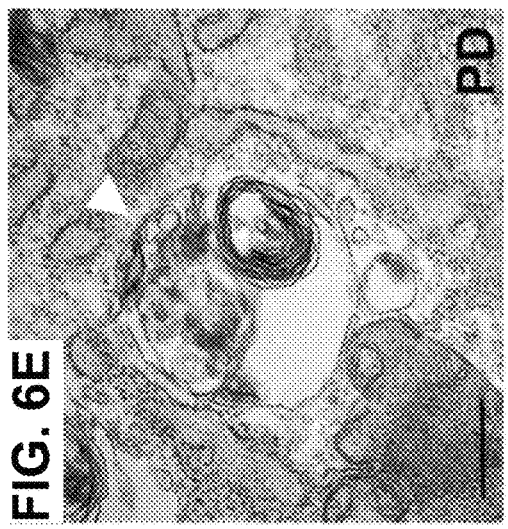

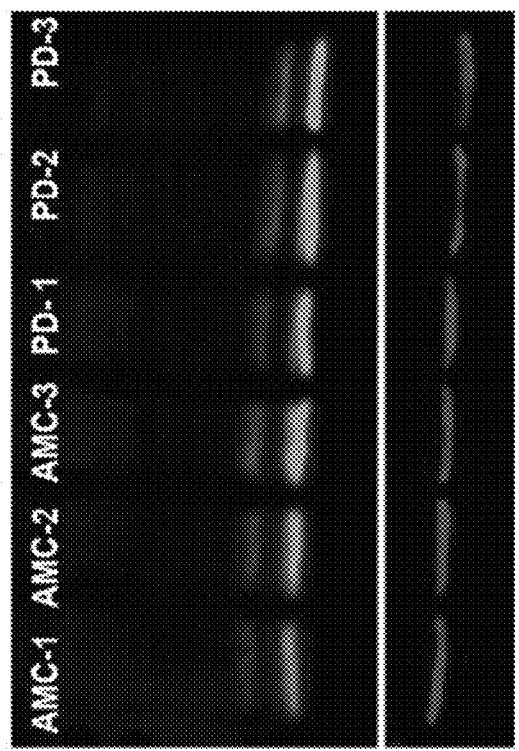
FIG. 6G) LC3-II
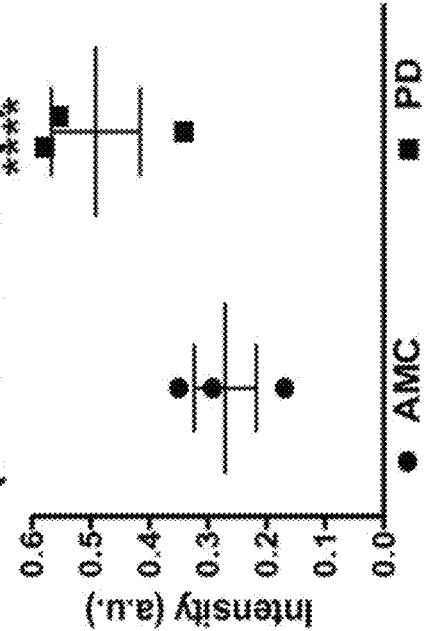
FIG. 6H) LC3-II (NH4Cl + leup)
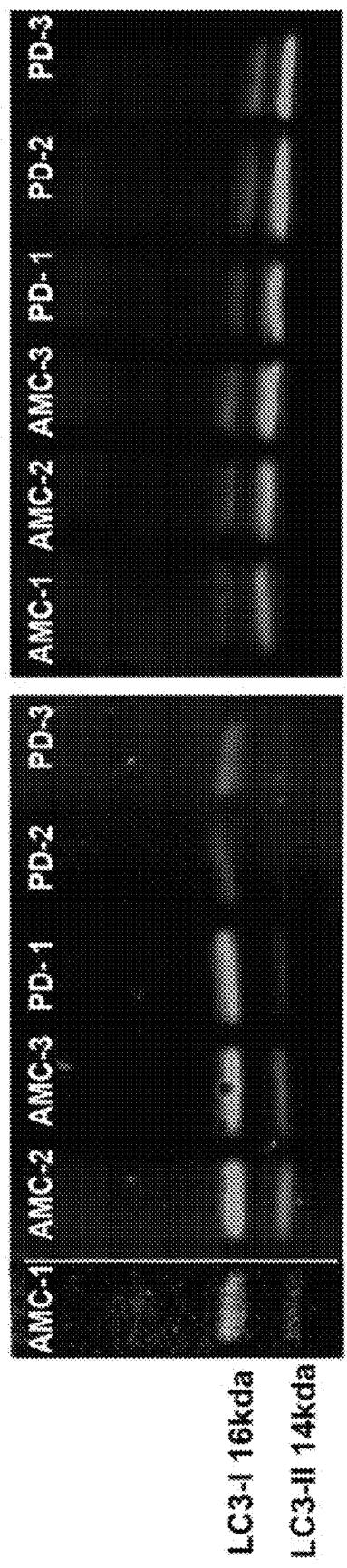
FIG. 6I) LC3-II
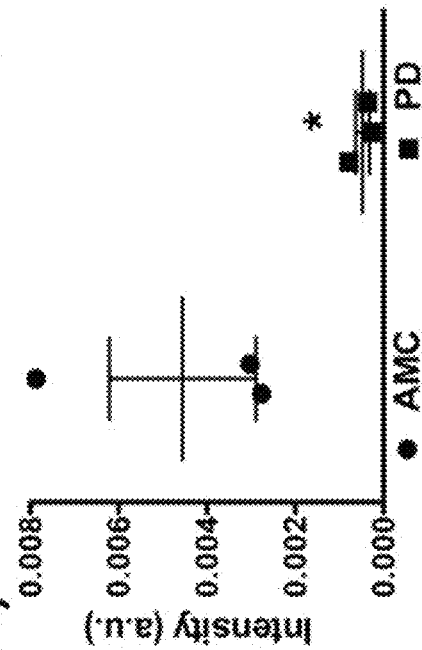
FIG. 6J) LC3-II (NH4Cl + leup)

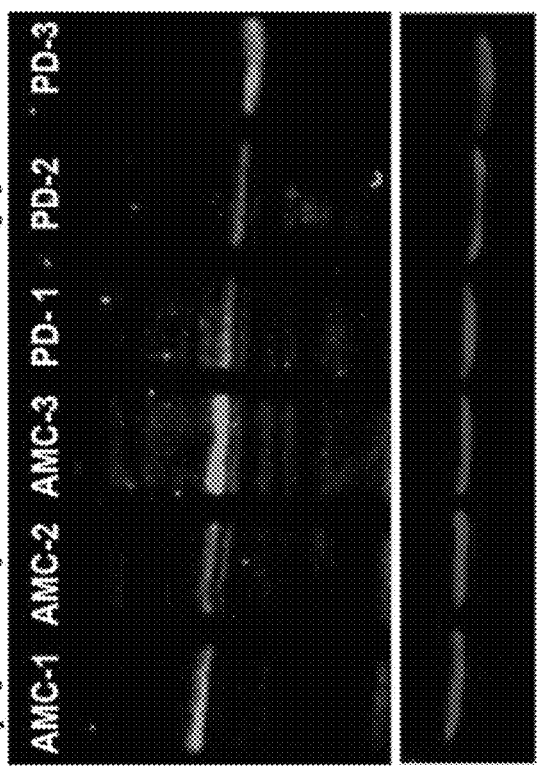
FIG. 6K) p62
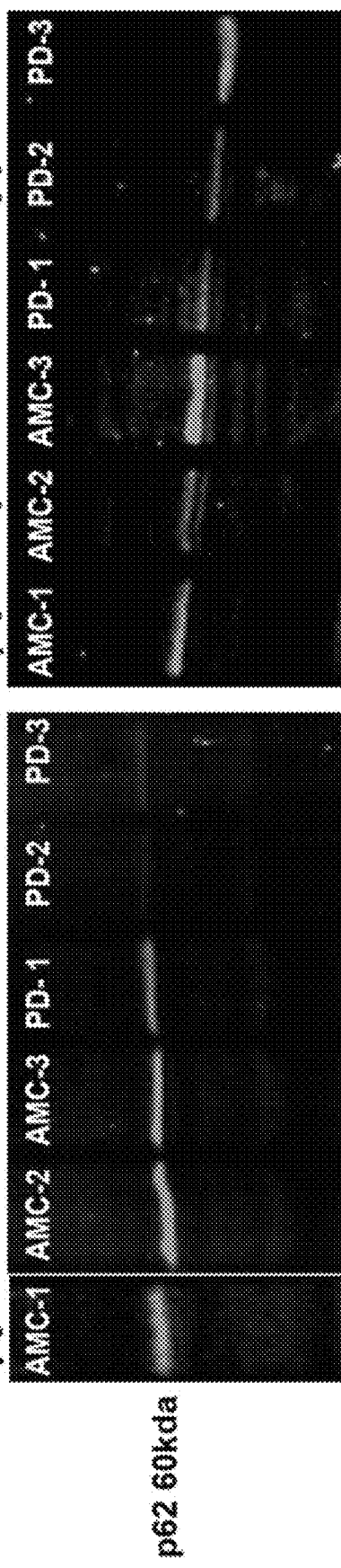
FIG. 6L) p62 (NH4Cl + leup)
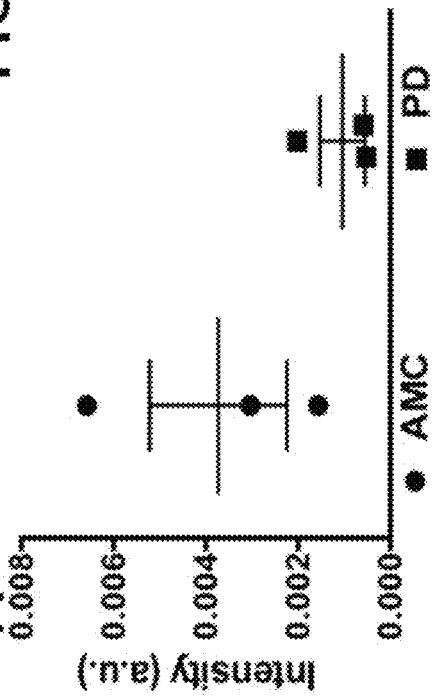
FIG. 6M) p62
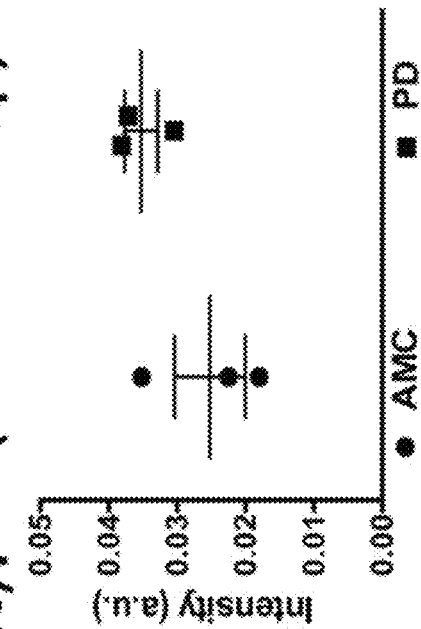
FIG. 6N) p62 (NH4Cl + leup)

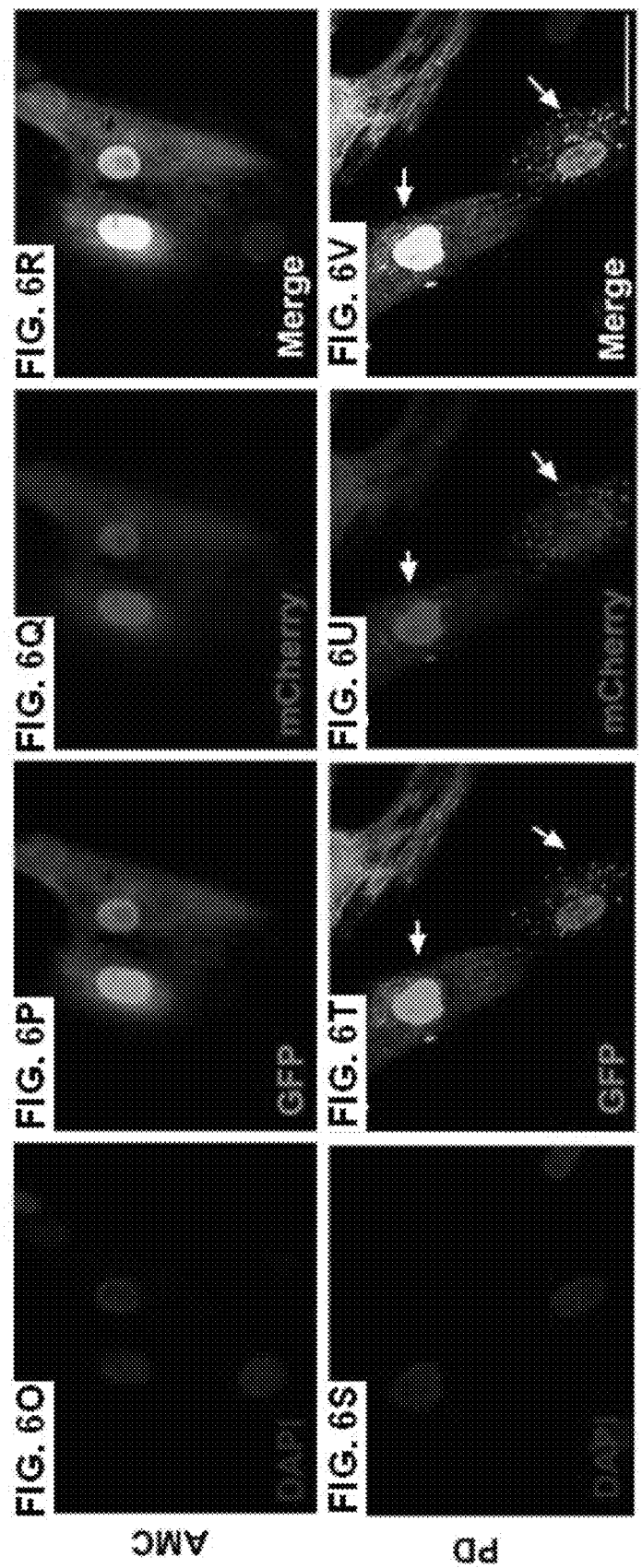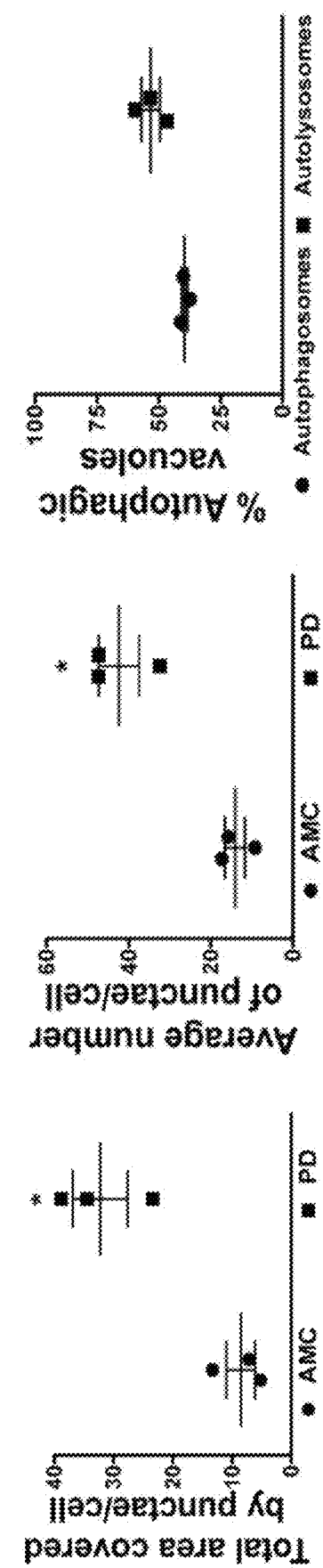

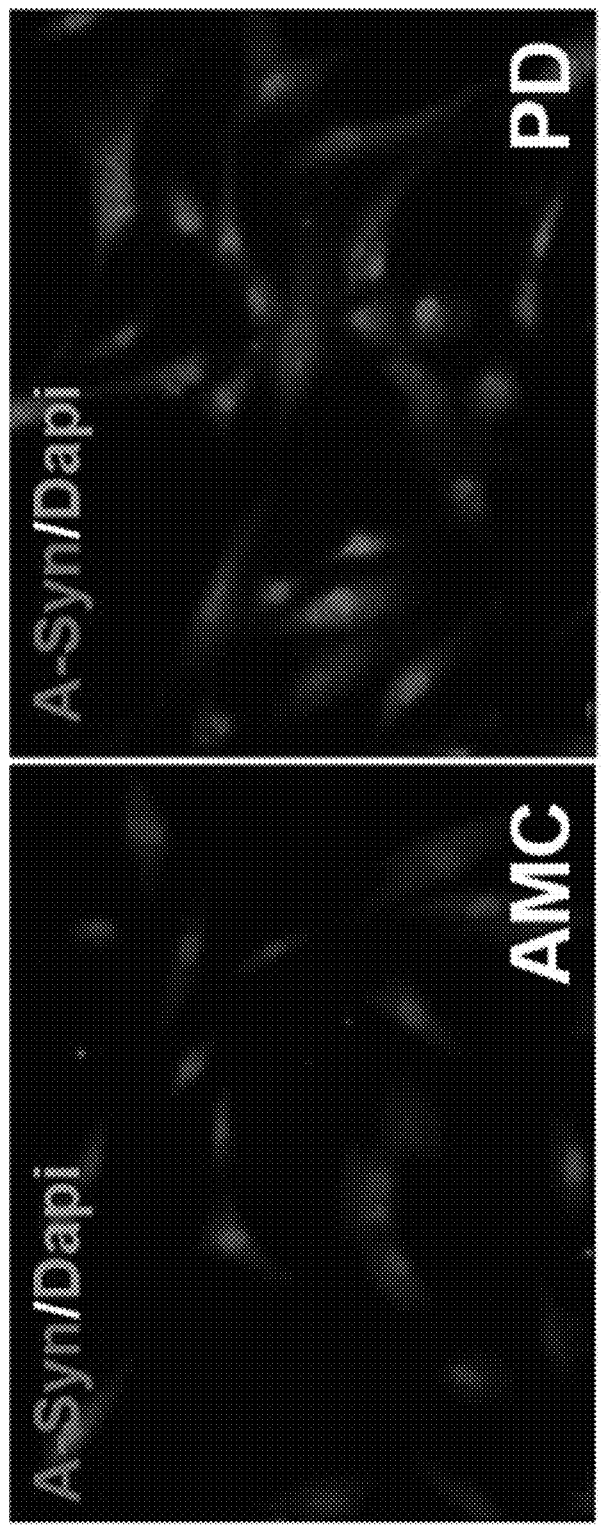
FIG. 7A
FIG. 7B
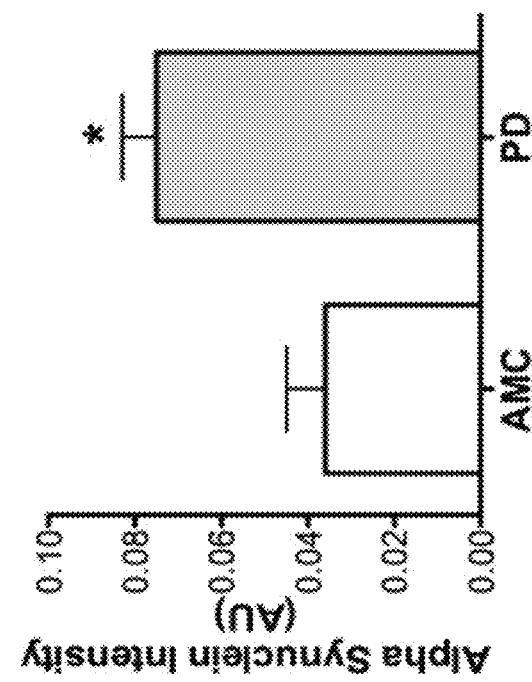
FIG. 7C

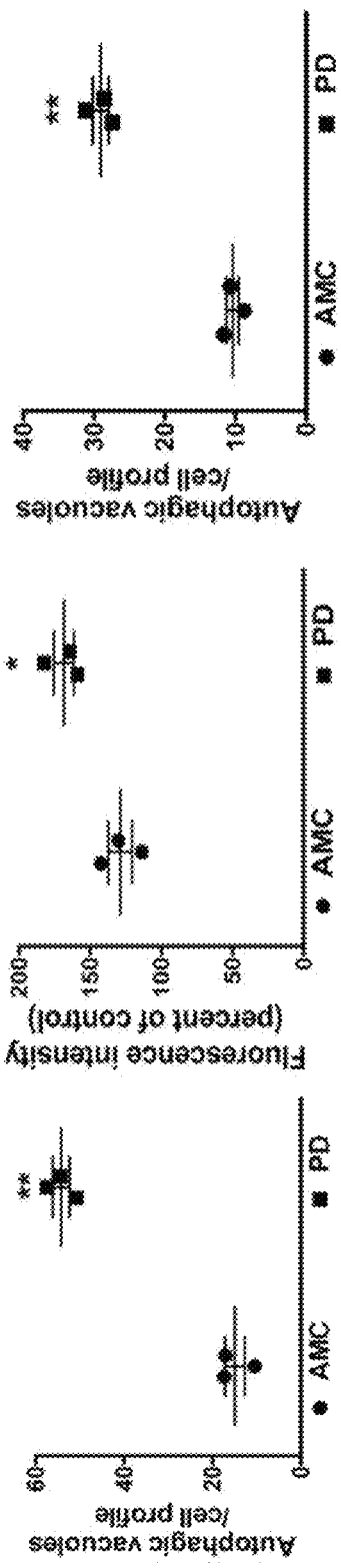
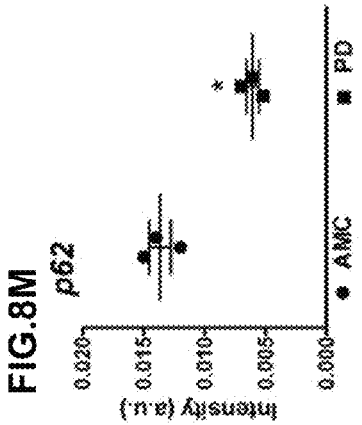
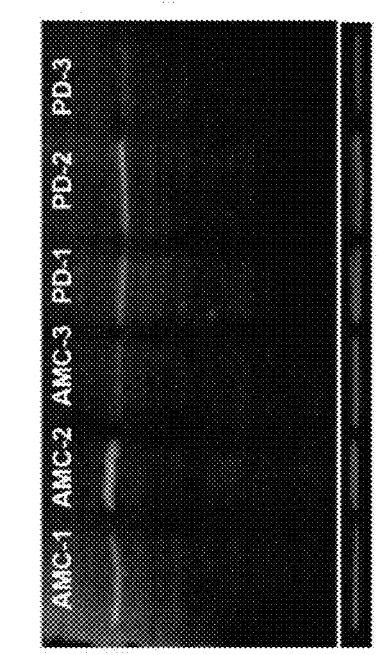

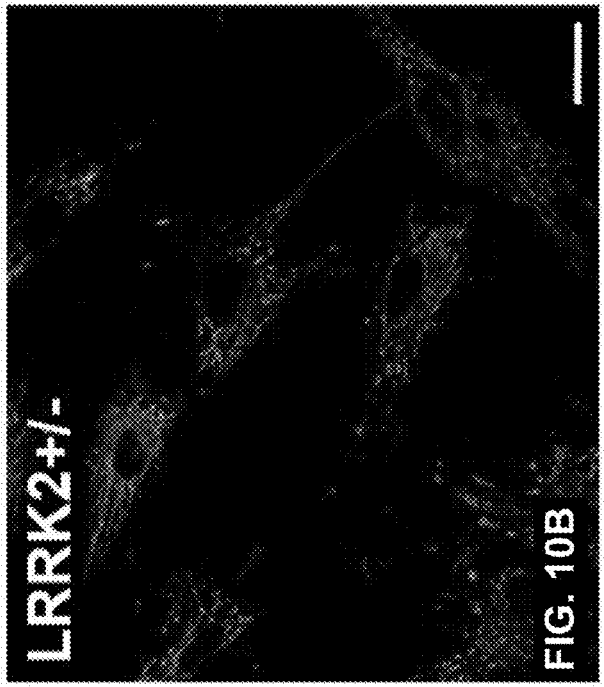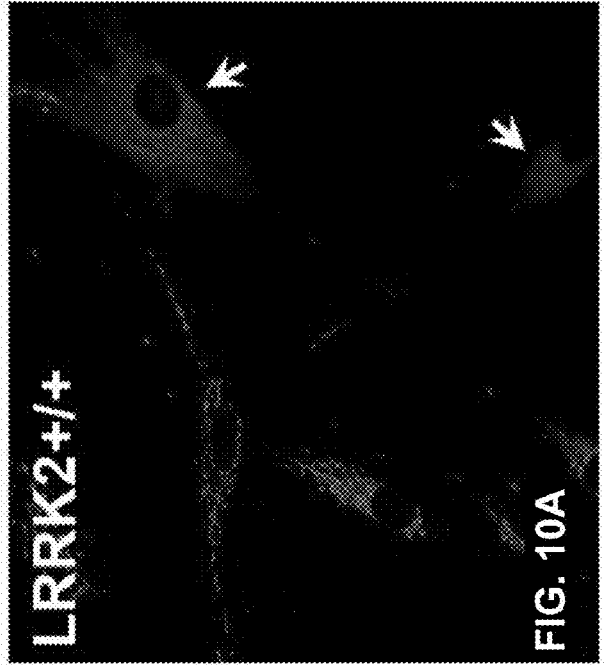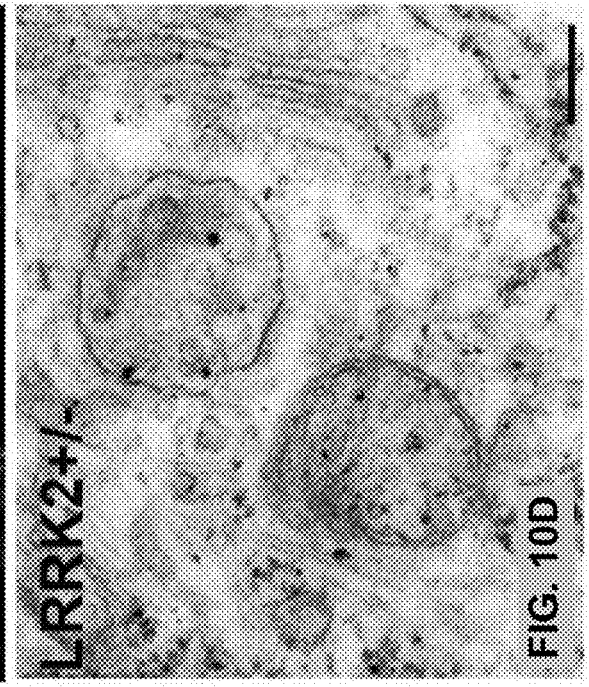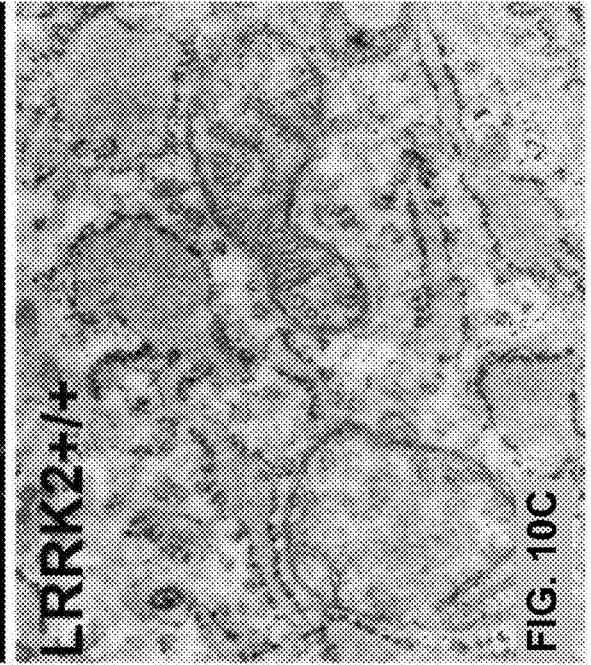

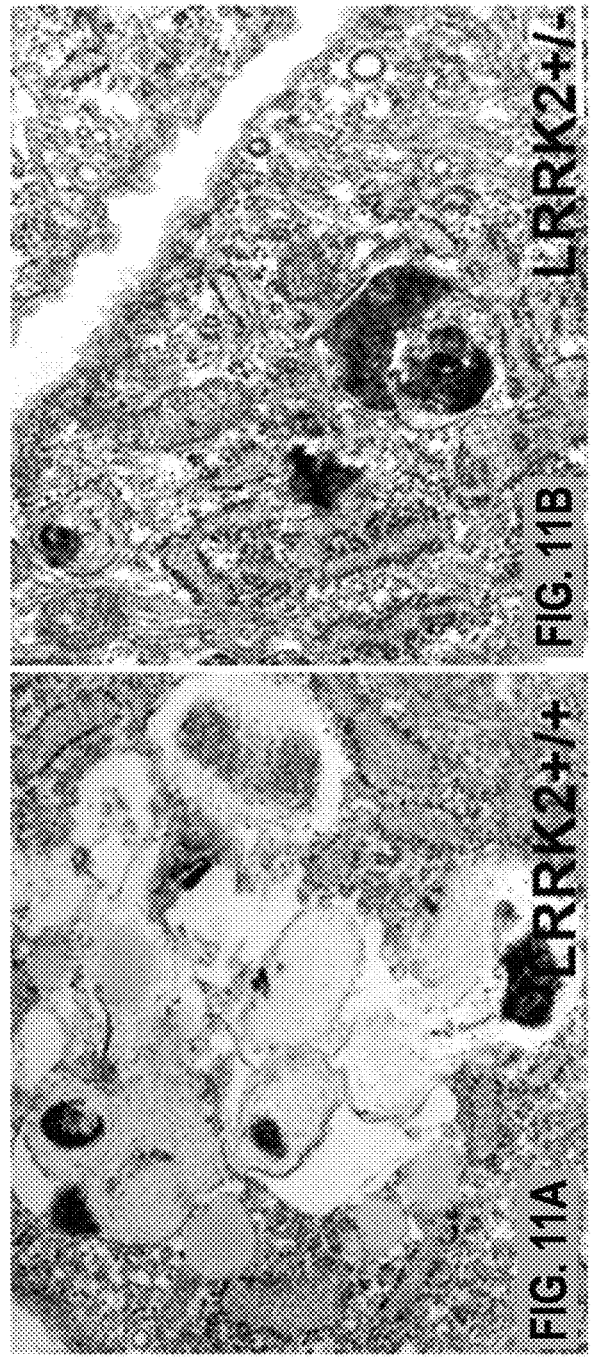
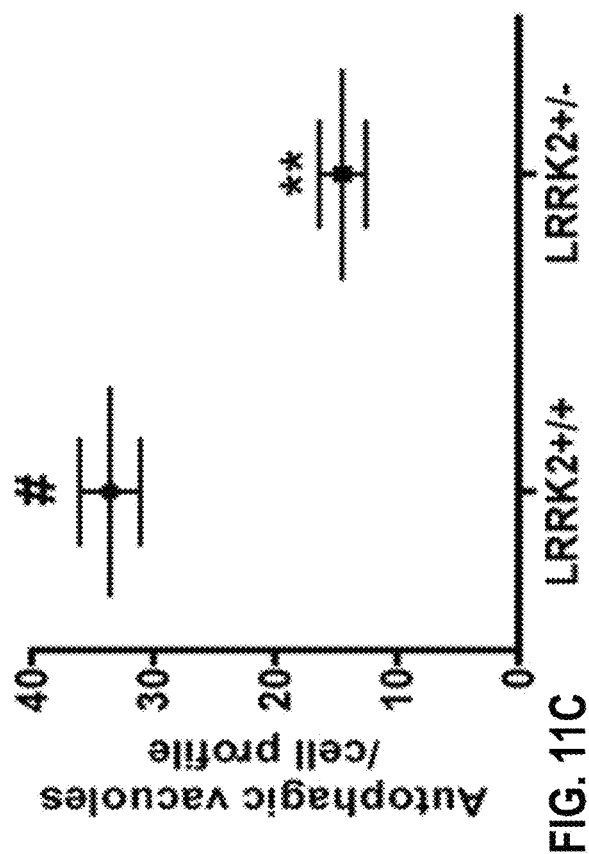
FIG. 11A  FIG. 11B  FIG. 11C

BIOMARKER PLATFORM FOR PARKINSON'S DISEASE USING PATIENT-DERIVED PRIMARY DERMAL FIBROBLASTS

CROSS REFERENCE

This application is a continuation and claims benefit of U.S. Non-Provisional patent application Ser. No. 16/162,242, filed Oct. 16, 2018, which claims benefit of U.S. Provisional Application No. 62/572,933, filed Oct. 16, 2017, the specification(s) of which is/are incorporated herein in their entirety by reference.

FIELD OF THE INVENTION

The present invention relates to diagnostic and prognostic biomarkers for Parkinson's disease, in particular, to skin fibroblasts as a patient-relevant model that captures fundamental PD molecular mechanisms.

BACKGROUND OF THE INVENTION

Parkinson's disease (PD) is a chronic age-related neurodegenerative disorder, which affects more than 6.5 million people worldwide. Although a small proportion of PD has clear genetic linkages, more than 90% of cases are deemed sporadic (or 'idiopathic')—meaning of unknown cause. A major issue faced by PD patients is that although symptomatic therapies are available, there are no current treatments that can slow or halt the progression of the disease. An important factor impeding therapeutic progress has been the inadequate understanding of PD etiopathogenesis, and its relatively late diagnosis which currently occurs in the clinic at an advanced stage when 60-70% of afflicted neurons have already degenerated (or are dysfunctional) and classical motor symptoms, such as tremor and rigidity, have already appeared. Moreover, even at this late stage, it is known that the sensitivity of PD clinical diagnosis in symptomatic patients is only about 90% or lower. Hence, there is a critical need for human models, which will allow for a robust investigation of how PD develops, and reliable biomarkers for early diagnosis of the disease.

It has been proposed that PD has a complex multifactorial etiology, involving many genetic and environmental factors, over the course of aging. However, the precise nature of these gene-environment interactions is not well understood, and constitutes an area of high scientific interest. Nevertheless, studies have indicated that such complex interactions may ultimately lead to a compromise in fundamental processes that maintain cellular homeostasis, such as mitochondrial function, redox balance, and protein quality control. In particular, interconnected molecular pathways causing mitochondrial dysfunction and impaired bioenergetics, oxidative stress due to excessive production of reactive oxygen species (ROS), and impaired protein degradation, especially through the ubiquitin-proteasome and autophagy-lysosome pathways, can act as common denominators of neuronal death in PD.

The discovery of biomarkers for (PD) is challenging due to the heterogeneous nature of this disorder, and a poor correlation between the underlying pathology and the clinically expressed phenotype. An ideal biomarker would inform on PD-relevant pathological changes via an easily assayed biological characteristic, which reliably tracks clinical symptoms. Human dermal (skin) fibroblasts are accessible peripheral cells that constitute a patient-specific system, which potentially recapitulates the PD chronological and epigenetic aging history. Fibroblasts offer an advantage in that they are accessible cells, which can be derived from PD-affected populations to provide a patient-specific culture system to study the disease. In particular, as a primary cell type, fibroblasts retain the specific environmental and aging history, and polygenic risk factors of the patient. Furthermore, although non-neuronal, fibroblasts make dynamic cell-to-cell contacts, similar to neurons, in culture.

Thus far, reports have focused predominantly on analyzing fibroblasts from genetic PD patients, and largely in the context of specific molecular processes of interest. In contrast, the present invention conducts a systematic, in-depth, and fine-grained analysis of the attributes of fibroblasts obtained from sporadic late-onset PD patients, with those from healthy age-matched control subjects. More specifically, the present invention analyzed cells from several viewpoints, including their growth dynamics and morphological characteristics, as well as mitochondrial function, redox homeostasis, and autophagy, which are core mechanisms known to be affected in PD pathogenesis.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

Patient-derived primary dermal fibroblasts are accessible peripheral cells that recapitulate the Parkinson's disease (PD) chronological and epigenetic aging history, and provide a useful system to study the disease. Here, the present invention utilized dermal fibroblasts from late onset sporadic and LRRK2+PD subjects and age-matched control subjects, and systematically examined the morphology, growth dynamics, viability, mitochondrial and autophagy-related function, as well as response to stress of these cells.

In some aspects, the present invention may feature a method for generating a Parkinson's disease (PD)-specific diagnostic biomarker profile. The method may comprise obtaining a non-neuronal biological sample from a patient, growing said biological sample in a medium, measuring growth dynamics, morphology, viability, as well as oxidative stress and mitochondrial and autophagic function of said biological sample to establish a baseline, exposing said biological sample in the medium to an external agent for a period of time to induce stress in said biological sample, and performing tests and assays on said stress-induced biological sample to determine growth dynamics, morphology, viability, oxidative stress, mitochondrial function, and autophagy function. The PD diagnostic biomarker profile may comprise data from the growth dynamics, morphology, viability, oxidative stress, mitochondrial function, and autophagy function. Preferably, the PD diagnostic biomarker profile can be compared to an age-matched reference biomarker profile to determine if a patient has PD.

In other aspects, the present invention may feature a method of identifying a subject in early stages of Parkinson's disease (PD) or tracking PD progression in the subject. The method may comprise obtaining a non-neuronal biological sample from the subject, growing said biological sample in a medium, and generating a PD diagnostic biomarker profile of said biological sample. In one aspect, the step of generating the PD diagnostic biomarker profile may comprise measuring growth dynamics, morphology, viability, as well as oxidative stress, mitochondrial and autophagic function of said biological sample, exposing said biological sample in the medium to an external agent for a period of time to induce stress in said biological sample, and performing tests and assays on said stress-induced biological sample to determine growth dynamics, morphology, viability, oxidative stress, mitochondrial function, and autophagy function. In further aspects, the PD diagnostic biomarker profile may be compared to a reference biomarker profile to determine if said subject is in the early stages of PD or to determine a progression of PD in the subject.

In one aspect, it was found that fibroblasts from PD patients were significantly ($p<0.05$) smaller and more circular than control cells. In terms of growth dynamics, PD fibroblasts grew faster and showed higher cell density at time of passage relative to the control cells. In addition, PD cells showed specific patterns of spatial organization in culture, which were different from control fibroblast lines. When the response of the fibroblasts to ultraviolet radiation (specifically UVA) induced stress was examined, higher reactive oxygen species (ROS) production, particularly mitochondrial ROS, was observed in PD cells compared to controls. To further analyze this effect, the PD and control lines were subjected to a mitochondrial stress test using the Seahorse Mito Stress Kit and Extracellular Flux analyzer. Data indicated that in comparison to control fibroblasts, respiratory control rate (RCR), proton leak, and coupling efficiency were negatively altered in the cells from individuals diagnosed with PD. Analysis of mitochondrial quantity and appearance showed lower levels and abnormal features in PD cells. Furthermore, given that increased expression of alpha-synuclein (α-syn), a substrate of autophagy, was observed in PD fibroblasts via immunocytochemistry, specific autophagy marker proteins (LAMP1, p62, LC3-I, LC3-II) were analyzed via immunoblot analysis. Autophagic vesicles were also analyzed through electron microscopy and fluorescence techniques. Data from these experiments suggest that autophagy may be impaired in the PD cells relative to controls.

One of the unique and inventive technical features of the present invention is the step of exposing the biological samples to an external agent, such as UV irradiation, to induce stress in said biological sample, such as peripheral fibroblasts. Without wishing to limit the invention to any particular theory or mechanism, it is believed that this technical feature advantageously allows for PD-related biological mechanisms to be explicitly expressed in the biological sample, e.g. in the peripheral fibroblasts. None of the presently known prior references or work has the unique inventive technical feature of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which:

FIGS. 2A-2M show growth and morphology differences between age-matched control (AMC) and PD fibroblasts. PD and AMC fibroblasts exhibited distinct growth patterns in culture (FIGS. 2A-2F). No differences in cell viability, assessed via a trypan blue assay, were noted between PD and AMC cultures (FIG. 2G). However, the number of days needed to reach 75% confluence (FIG. 2H) was lower in the PD cultures. Also correlatively, a higher total cell count at the 75% confluence stage (FIG. 2I) and a higher population doubling level (FIG. 2J) was noted in the PD cultures. The density of the cultures was also quantified via CellProfiler software. FIG. 2K shows how the software outlines each "cell object" based on fluorescence staining to finally measure cellular density. Comparative analysis of density between AMC and PD in terms "percentage of Neighbor Touching" and "number of Adjacent Neighbors" is shown in FIGS. 2L, 2M. Scale Bars: FIGS. 2A-2C=100 μm, FIGS. 2D-2F=50 μm. $*p<0.05$, $p<0.01$, $**p<0.0001$; Mean±SEM, Unpaired t-tests with Welch's correction, n=3 independent PD and AMC lines.

FIGS. 3A-3G show cellular size and shape analysis of PD and AMC fibroblasts. FIG. 3A shows a sample CellProfiler image showing outlines of "cell objects" according to fluorescence Phalloidin and Dapi stains and the list of parameters used to quantify size and shape. Quantification of cellular area (FIG. 3B), perimeter (FIG. 3C), maximum ferret (FIG. 3D, measuring the predicted length of the object across planes), minimum ferret (FIG. 3E, measuring the predicted width of each object across planes), eccentricity (FIG. 3F, arbitrary value for roundness), and form factor (FIG. 3G, arbitrary value on how defined the outline of an object is) in PD and AMC cultures. $*p<0.05$, $p<0.01$, $*p<0.001$, Mean±SEM, unpaired t-tests with Welch's correction, n=4-5 independent PD and AMC lines.

FIGS. 4A-4J show reduced viability and increased oxidative stress in PD cultures after UVA. FIG. 4A is an exemplary schematic of the experimental design. Baseline MTT and DCF analysis is depicted in FIGS. 4B and 4C. Phase contrast images of PD and AMC cells before and after UVA treatment is shown in FIGS. 4D-4G. Comparative viability of PD and AMC cells after UVA via an MTT assay is depicted in FIG. 4H. Quantification of DCF-DA (FIG. 4I) and Mitosox (FIG. 4J) fluorescence post-UVA, shows greater ROS production in PD lines. Scale Bars: FIGS. 4B-4E=200 μm. $*p<0.05$, $p<0.01$, $*p<0.001$, FIGS. 4B-4C: unpaired t tests with Welch's correction, FIGS. 4H-4J: One way ANOVA with Bonferroni's post-hoc test, Mean±SEM, n=3-4 independent PD and AMC lines.

FIGS. 5A-5N show mitochondrial dysfunction in PD fibroblasts. Rhodamine 123 stained fibroblasts showing bright and typical mitochondrial network morphology in AMC cells (FIGS. 5A-5B) but low intensity fragmented mitochondria in PD fibroblasts (FIGS. 5C-5D). FIGS. 5B and 5D are maximum intensity projection images from confocal z-stacks. Rhodamine 123 quantification is in FIG. 5E. Electron micrograph displaying normal mitochondrial morphology in AMC cells is depicted in FIG. 5F. PD cultures on the other hand showed abnormal features such as mitophagy (FIG. 5G), mitochondria lacking cristae (FIG. 5H), and collapsed mitochondria (FIG. 5I). Quantification of collapsed mitochondria is in FIG. 5J. Schematic depicting the steps of the mitostress test is in FIG. 5K. RCR is significantly lower on average (FIG. 5L), and PL is significantly higher, in PD cells (FIG. 5M). Relatively lower CE is seen in PD lines on average (FIG. 5N). Scale Bars: FIGS. 5A-5D=40 μm; FIGS. 5F-5I=250 nm. $*p<0.05$, $p<0.01$, $**p<0.0001$; Mean±SEM, unpaired t tests with Welch's correction (FIG. 5E) and two way ANOVA with Tukey's post-test (FIGS. 5L-5N); Median±interquartile range, Mann Whitney U-test (FIG. 5J); n=3-4 independent PD and AMC lines.

FIGS. 6A-6Y shows increased autophagy at baseline in PD fibroblasts. FIGS. 6A-6B (arrows) shows electron micrographs of AMC fibroblasts with some autophagic vesicles. However, PD fibroblasts contained significantly more autophagic vesicles (FIG. 6C, arrows). A classic double-membrane autophagosome with cargo (FIG. 6D, black arrowhead) and autolysosome with degradative material (FIG. 6E, white arrowhead), seen in PD fibroblasts. FIG. 6F shows EM quantification of autovesicles. Western blots showing significantly lower protein expression of autophagy marker LC3-II in PD fibroblasts (FIGS. 6G, 6I) and p62 (FIGS. 6K, 6M) at baseline. Normalization occurred to β-Actin. LC3-II and p62 expression (flux) increased upon blocking of degradation via a combination of NH4Cl and Leupeptinin especially PD cell lines (FIGS. 6H, 6J, 6L, 6N). Fluorescence tracking of autophagic flux in Ad-mCherry-GFP-LC3 transfected AMC fibroblasts is shown in FIGS. 6O-6V with quantification in FIGS. 6W-6Y. Green puncta represent autophagosomes whereas red puncta represent autolysosomes. Scale Bars: FIGS. 6A-6E=500 μm, FIGS. 6O-6V=50 μm. *$p<0.05$, $p<0.01$, **$p<0.0001$; Mean±SEM, unpaired tests with Welch's correction, n=3 independent PD and AMC lines.

FIGS. 7A-7C show greater immunocytochemical expression of the PD-relevant protein alpha-synuclein (α-synuclein) in PD fibroblasts as compared to AMC cells. FIGS. 7A and 7B show immunocytochemical staining of AMC and PD fibroblasts, respectively. FIG. 7C show CellProfiler quantification.

FIGS. 8A-8M show increased autophagy in PD fibroblasts after UVA stress. FIG. 8A is an exemplary schematic of the experimental design. Electron micrograph of a UVA-treated AMC cell showing accumulation of autophagic vesicles is in FIG. 8B, arrows. Widespread accumulation of autophagic vesicles and lipofuscin structures is seen in PD cells in FIG. 8C, arrows. Lipofuscin-like dense structures are seen in PD cells in FIG. 8D, white arrows, and high magnification view in FIG. 8E. These are quantified in FIG. 8I. A high magnification image of a typical large autophagolysosome in a PD cell in FIG. 8F, black arrowhead. EM Quantification is in FIG. 8G. Flow cytometric analysis showed higher autofluorescence in PD lines after UVA, corresponding to presence of lipofuscin structures (FIG. 8H). Western blotting indicated higher LC3-II expression in the PD lines (FIGS. 8J, 8K), and lower p62 expression, suggesting increased autophagic degradation (FIGS. 8L, 8M). Scale Bars: FIG. FIG. 8B-8F=500 nm. *$p<0.05$, **$p<0.01$, FIG. 8G—one-way ANOVA with Bonferroni's post-hoc test, FIG. 8I—Mean±SEM, unpaired t-tests with Welch's correction, n=3 independent PD and AMC lines.

FIGS. 9A, 9B=100 μm; FIGS. 9C, 9D=50 μm. (#$p<0.05$, ##$p<0.01$, ###$p<0.0001$ compared to sporadic PD; *$p<0.05$, $p<0.01$, **$p<0.0001$ compared to LRRK2+/+; Mean SEM, unpaired t tests with Welch's correction.)

FIGS. 10A-10G show LRRK2 cells with significant changes in ROS production and mitochondrial morphology. LRRK2 cells showed reduced Rhodamine 123 fluorescence (particularly missing in several LRRK2+/+ cells, arrows) and fragmented mitochondrial morphology (FIGS. 10A, 10B, 10F). These LRRK2+/+ cells also had greater numbers of collapsed mitochondria (FIGS. 10C, 10D, 10G) and increased ROS levels compared to other PD cells (FIG. 10E). Scale Bars: FIGS. 10A, 10B=0 μm; FIGS. 10C, 10D=250 nm. (#$p<0.05$, ##$p<0.01$, ###$p<0.0001$ compared to sporadic PD; *$p<0.05$, $p<0.01$, **$p<0.0001$ compared to LRRK2+/+; Mean±SEM, unpaired t tests with Welch's correction.)

FIGS. 11A-11C show LRRK2 cells exhibiting increased autophagy. FIGS. 11A and 11B depict EM level accumulations of autophagic vesicles in the LRRK2+/+ and LRRK2+/− cells. The graph in FIG. 11C indicates that the LRRK2+/+ cells have a higher concentration of autophagic vesicles compared to other sporadic and LRRK2+/−PD cells. Scale Bars: FIGS. 11A, 11B=500 nm. (#$p<0.05$ compared to sporadic PD; **$p<0.01$ compared to LRRK2+/+; Mean±SEM, unpaired t tests with Welch's correction.)

DESCRIPTION OF PREFERRED EMBODIMENTS

The development of clinically relevant biomarkers poses an enormous challenge in Parkinson's disease (PD). PD's unknown multifactorial etiology, protracted course across aging, heterogeneity, and fluctuating clinical phenotype, make it a difficult disorder to diagnose. As a result, idiopathic PD usually remains unrecognized until late in its progression when most of the brain's affected neurons have already been lost, and classical motor symptoms such as tremor and rigidity have already appeared. Moreover, even at this late stage, it is known that the sensitivity of PD clinical diagnosis in symptomatic patients is only about 90% or lower. Hence there is a critical need for biomarkers that can reliably identify early stages of PD, and stratify this heterogeneous disease into clinical subtypes, so that treatments can effectively be applied.

Figure 1A:
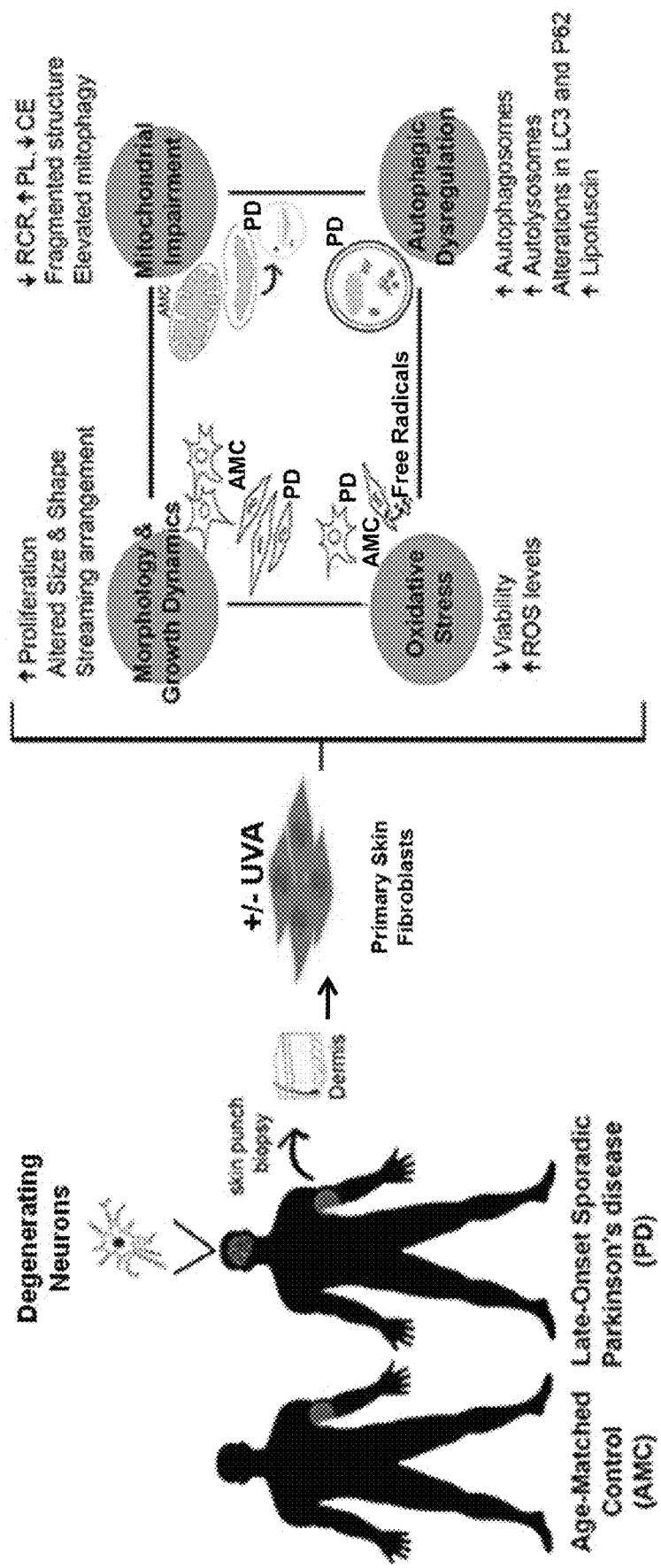
FIGS. 1A-1B show non-limiting flow diagrams of embodiments of the present invention.
Figure 1B:
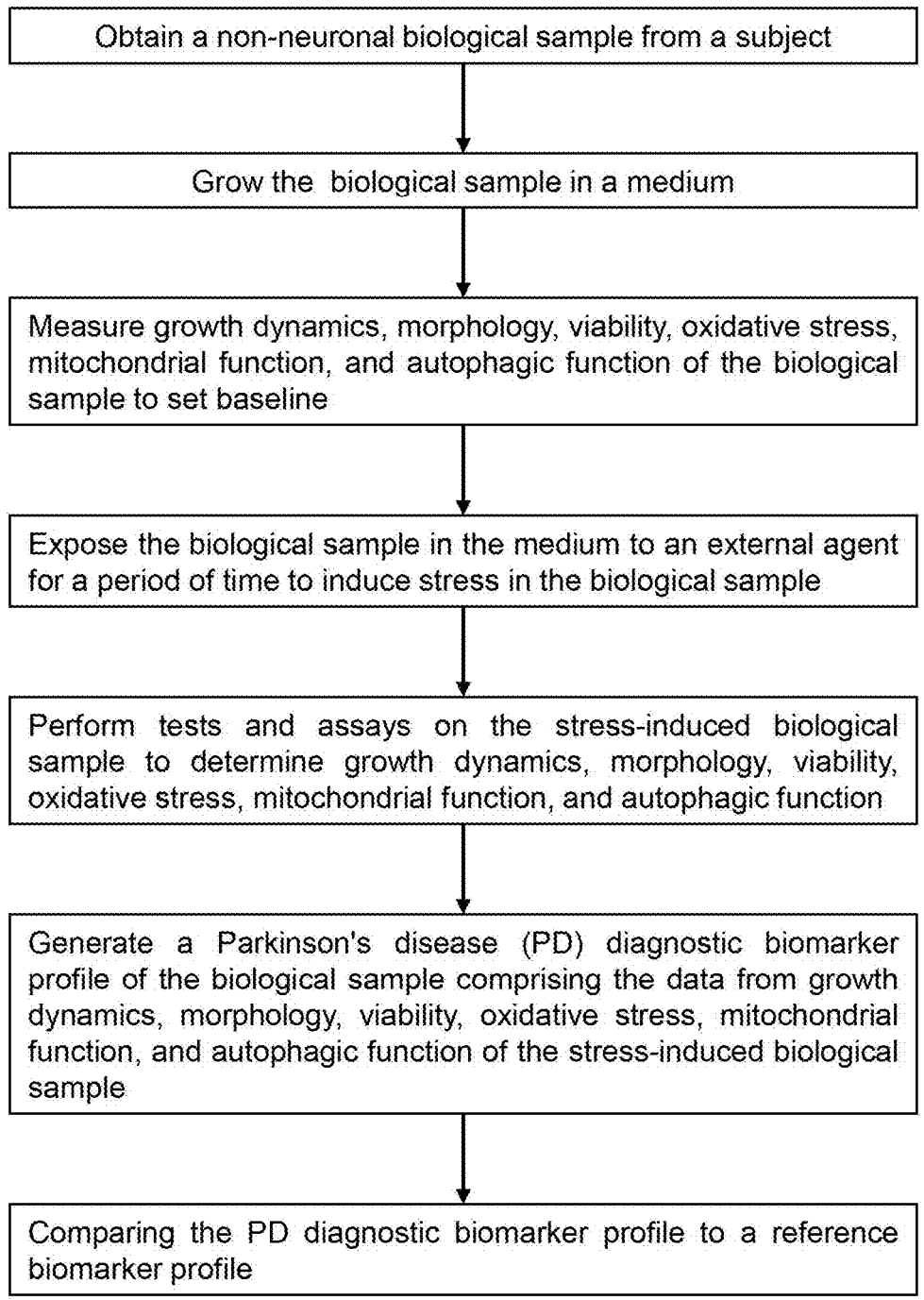

Referring now to FIGS. 1A-1B, in some embodiments, the present invention features a method of generating a diagnostic biomarker profile for Parkinson's disease (PD). The method may comprise obtaining a non-neuronal biological sample from a patient, growing said biological sample in a medium, measuring growth dynamics, morphology, viability, as well as oxidative stress and mitochondrial and autophagic function of said biological sample. Alternatively or in combination, the method may include exposing said biological sample in the medium to an external agent for a period of time to induce stress in said biological sample, and performing tests and assays on said stress-induced biological sample to determine growth dynamics, morphology, viability, oxidative stress, mitochondrial function, and autophagy function. In one embodiment, the PD diagnostic biomarker profile may comprise data from the growth dynamics, morphology, viability, oxidative stress, mitochondrial function, and autophagy function. Preferably, the PD diagnostic biomarker profile can be compared to a reference biomarker profile to determine if said patient has PD.

According to another embodiment, the present invention features a method of diagnosing, monitoring, prognosing, or tracking progression of Parkinson's disease (PD) in a subject. The method may comprise obtaining a non-neuronal biological sample from the subject, growing said biological sample in a medium, and generating a PD diagnostic biomarker profile of said biological sample.

In one embodiment, the step of generating the PD diagnostic biomarker profile may comprise measuring growth dynamics morphology, viability, oxidative stress, and mitochondrial and autophagic function of said biological sample to generate PD diagnostic biomarker profile. Alternatively or in combination, the step of generating the PD diagnostic biomarker profile may comprise exposing said biological sample in the medium to an external agent for a period of time to induce stress in said biological sample, and performing tests and assays on said stress-induced biological sample to determine growth dynamics, morphology, viability, oxidative stress, mitochondrial function, and autophagy function.

In other embodiments, the step of generating the PD diagnostic biomarker profile may comprise measuring growth dynamics, morphology, viability, as well as oxidative stress and mitochondrial and autophagic function of said biological sample to establish a baseline, exposing said biological sample in the medium to an external agent for a period of time to induce stress in said biological sample, and performing tests and assays on said stress-induced biological sample to determine growth dynamics, morphology, viability, oxidative stress, mitochondrial function, and autophagy function.

In some embodiments, the initial step of measuring growth dynamics morphology, viability, oxidative stress, and mitochondrial and autophagic function of said biological sample establishes a baseline, or baseline profile. Without wishing to limit the present invention, a comparison of results from the baseline, (that is without stress-induction) of PD cells to healthy reference control cells (also without stress-induction) may itself be sufficient enough for diagnosis. Thus, in this embodiment, the baseline profile is also the PD diagnostic biomarker profile.

However, PD is a heterogeneous disease which may be expressed differently in different patients. Hence, in other embodiments, it may be necessary to expose the cell samples to stress and compare the stress-induced PD cells to the stress-induced control cells for diagnosis/prognosis of the disease. The PD diagnostic biomarker profile may comprise data from growth dynamics, morphology, oxidative stress, viability, mitochondrial function, and autophagy function of said stress-induced biological sample. Without wishing to limit the present invention, it may be possible that stress is needed to 'uncover' PD in the early stages of the disease.

In further embodiments, the methods described herein may further comprise comparing the PD diagnostic biomarker profile to a reference biomarker profile. Without wishing to limit the present invention, by comparing the PD diagnostic biomarker profile to the reference biomarker profile, it could be determined if the subject is at risk of PD, if the subject has PD, or what stage of PD. For example, the method may determine if the subject is in the early stages of PD or later stages of PD in the subject. Without wishing to limit the invention to a particular theory or mechanism, the method advantageously allows for early-stage detection of PD in the subject. Further still, the method advantageously allows for monitoring of PD progression in the subject.

According to another embodiment, the present invention may include a method of treating Parkinson's disease (PD) in a subject in need thereof. The method may comprise obtaining a non-neuronal biological sample from the subject, growing said biological sample in a medium, measuring growth dynamics morphology, viability, oxidative stress, and mitochondrial and autophagic function of said biological sample to generate PD diagnostic biomarker profile, comparing the PD diagnostic biomarker profile to a reference biomarker profile, and administering a therapeutic treatment to the subject. Without wishing to limit the invention, by comparing the PD diagnostic biomarker profile to a reference biomarker profile, a stage of PD in the subject can be determined, or the state of PD in the subject can be monitored. In one embodiment, depending on the stage or state of PD in the subject, the subject may be prescribed and administered an appropriate therapeutic treatment. Non-limiting examples of PD treatments include levodopa, dopamine agonists, MAO-B inhibitors, COMT inhibitors, amantadine, anticholinergics, and deep brain stimulation surgery. In further embodiments, the treatment method may include, prior to the step of measuring, exposing said biological sample in the medium to an external agent for a period of time to induce stress in the biological sample. Preferably, for comparison, the reference biomarker profile is obtained from a healthy control sample that has also been stress-induced. In an alternative embodiment, the biological sample is not stress-induced, and the reference biomarker profile is obtained from a healthy, non-stressed control sample.

As used herein, the terms "treat", "treating", or "treatment" refer to both therapeutic treatment and prophylactic or preventative measures, with the objective of preventing, reducing, slowing down (lessen), inhibiting, or eliminating an undesired physiological change, symptom, disease, or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented or onset delayed. Optionally, the subject or patient may be identified (e.g., diagnosed) as one suffering from the disease or condition prior to administration of a treatment.

In some embodiments, the present invention may be used to guide future clinical trials in testing novel drugs for their therapeutic potential in treating Parkinson's disease. For example, a screening process would determine if a drug can revert PD fibroblast (with or without stress) to the control/reference profile and/or stratify patients that are suitable for certain drugs in clinical trials. Potential therapeutic drugs can be tested in each patient's fibroblast system and if the patient's biomarkers improve, then the patient may potentially respond to the drug better and therefore should be treated with the drug and/or selected for a clinical trial.

In one embodiment, a method of screening a drug for its safety and efficacy in treating Parkinson's disease (PD) may comprise obtaining a non-neuronal biological sample from a subject with PD, growing said biological sample in a medium, measuring growth dynamics morphology, viability, oxidative stress, and mitochondrial and autophagic function of said biological sample to generate PD diagnostic biomarker profile, comparing the PD diagnostic biomarker profile to a reference biomarker profile, and administering the drug to the sample. After drug administration, the method further comprises the steps of obtaining another biological sample from the PD subject, growing the sample in a medium, measuring growth dynamics morphology, viability, oxidative stress, and mitochondrial and autophagic function to generate another PD diagnostic biomarker profile, and comparing this subsequent PD diagnostic biomarker profile to the reference biomarker profile. Without wishing to limit the present invention, the drug can be determined to be suitable for treating PD if the drug demonstrates that it can improve or revert the PD diagnostic biomarker profile to the reference biomarker profile. Examples of the drug include, but are not limited to, levodopa, dopamine agonists, MAO-B inhibitors, COMT inhibitors, amantadine, anticholinergics. In one embodiment, the method may further comprise exposing said biological sample in the medium to an external agent for a period of time prior to the measuring step so as to induce stress in the biological sample. Preferable, the stress-induced biological sample is compared to a reference biomarker profile obtained from a healthy control sample that has also been stress-induced. In an alternative embodiment, the biological sample is not stress-induced, and the reference biomarker profile is obtained from a healthy, non-stressed control sample.

According to another embodiment, the present invention features a method of screening a subject for a drug that treats Parkinson's disease (PD). In one embodiment, the subject may be diagnosed with PD. In some embodiments, the method may comprise obtaining from the subject a fibroblast sample comprising fibroblast cells, generating a PD biomarker profile, comparing the PD biomarker profile to a reference biomarker profile, administering the drug to the fibroblast sample, generating a subsequent PD biomarker profile for the fibroblast sample administered with the drug, and comparing the subsequent PD biomarker profile to the initial biomarker profile, the reference biomarker profile, or both. Without wishing to limit the invention, the subject may be selected to receive treatments of the drug if the PD biomarker profile of the subject's fibroblast cells shows improvement after administration of the drug. For instance, if the PD biomarker profile improves over the initial PD biomarker profile or if the PD biomarker profile reverts to the reference biomarker profile, then the subject may be selected to receive treatments of the drug. Examples of the drug include, but are not limited to, levodopa, dopamine agonists, MAO-B inhibitors, COMT inhibitors, amantadine, anticholinergics.

In one embodiment, the PD biomarker profile can be generated by growing said fibroblast sample in a medium and measuring growth dynamics morphology, viability, oxidative stress, and mitochondrial and autophagic function of said fibroblast sample. In some embodiments, the PD biomarker profile may comprise data from growth dynamics, morphology, viability, oxidative stress, mitochondrial function, and autophagy function of said fibroblast sample from the subject. Similarly, the reference biomarker profile may comprise data from growth dynamics, morphology, viability, oxidative stress, mitochondrial function, and autophagy function of a healthy fibroblast control sample. In other embodiments, the step of generating the PD biomarker profile may further comprise exposing the fibroblast sample in the medium to an external agent for a period of time prior to the measuring step. The external agent can induce stress in said fibroblast sample. The reference biomarker profile may be obtained from a healthy fibroblast control sample that has also been stress-induced by an external agent. Alternatively, the fibroblast sample may not be stress-induced, and the reference biomarker profile is obtained from a healthy, non-stressed fibroblast control sample.

In other embodiments, the present invention provides a kit for diagnosing, monitoring, prognosing, or tracking progression of Parkinson's disease (PD). The kit may comprise a growing medium, a stress-inducing agent, one or more reference biomarker profiles, and instructions. The growing medium in configured for use in growing a non-neuronal biological sample, such as skin fibroblasts. The stress-inducing agent may be a UV radiation source for inducing stress in the biological sample that is growing in the medium. In some embodiments, the instructions may include directions for generating a PD diagnostic biomarker profile of the sample. In other embodiments, the instructions may comprise measuring dynamics, morphology, viability, as well as oxidative stress and mitochondrial and autophagic function of said biological sample. Alternatively or in combination, the instructions may comprise exposing said biological sample in the medium to an external agent for a period of time to induce stress in said biological sample, and performing tests and assays on said stress-induced biological sample to determine growth dynamics, morphology, viability, oxidative stress, mitochondrial function, and autophagy function. In one embodiment, the PD diagnostic biomarker profile may comprise data from growth dynamics, morphology, viability, oxidative stress, mitochondrial function, and autophagy function. The instructions may further comprise comparing the PD diagnostic biomarker profile to one of the reference biomarker profiles, preferably one that is age-matched. Without wishing to limit the invention, significant deviations in the PD diagnostic biomarker profile from the reference biomarker profile may be indicative of Parkinson's disease, as well as the stage of PD.

In still other embodiments, the present invention may feature a system for diagnosing, monitoring, prognosing or staging Parkinson's disease (PD) in a subject. The system may comprise a non-neuronal biological sample from the subject, a growing medium for growing the biological sample in said medium, an external agent for inducing stress in said biological sample, and one or more reference biomarker profiles. A PD diagnostic biomarker profile may be generated from the biological sample that has been grown in the medium and exposed to the stress-inducing external agent. The PD diagnostic biomarker profile may comprise data from growth dynamics, morphology, viability, oxidative stress, mitochondrial function, and autophagy function. The PD diagnostic biomarker profile may be compared to one of the reference biomarker profiles, preferably age-matched, in order to determine if the subject is at risk of PD, if the subject has PD, or the stage of PD.

In another embodiment, the system may include a processing unit comprising a processor and a non-transitory memory storage. The memory can store the one or more reference biomarker profiles as well as instructions that, when executed by the processor, cause the processor to perform operations. The operations may comprise receiving an input that includes the PD diagnostic biomarker profile, analyzing and comparing the PD diagnostic biomarker profile to one of the stored reference biomarker profiles, and outputting a result from said analysis. In the analysis, if there are significant deviations in the PD diagnostic biomarker profile as compared to the reference biomarker profile, they may be indicative of Parkinson's disease, as well as a stage thereof. In some embodiments, the processing unit may be configured to present the results on a display or to transmit the results to another computing device.

Consistent with the embodiments herein, the step of measuring growth dynamics may comprise measuring cell densities, spatial arrangement, number of adjacent neighbors, and population doubling time. In another embodiment, the step of measuring morphology may comprise measuring cell size and shape. For example, measuring cell size may comprise measuring cell area, perimeter, and feret diameters. As another example, measuring cell shape may comprise measuring eccentricity and form factor.

Consistent with the embodiments herein, the step of performing tests and assays on said biological sample to determine oxidative stress may comprise measuring reactive oxygen species (ROS) levels and mitochondria-specific ROS levels. In other embodiments, the step of performing tests and assays on said biological sample to determine mitochondrial function may comprise analyzing fibroblast mitochondria levels and mitochondria appearance. In further embodiments, the step of performing tests and assays on said biological sample to determine autophagy function may comprise detecting a presence of autophagic vesicles and structures and measuring levels thereof. In yet further embodiments, the step of performing tests and assays on said biological sample to determine autophagy function may comprise detecting expression of autophagy marker proteins such as, for example, alpha-synuclein, LAMP1, p62, LC3-I, and LC3-II.

Consistent with the embodiments herein, the reference biomarker profile may be obtained from a biological sample from a healthy age-matched control subject, referred to herein as AMC. In some embodiments, the AMC may be grown in a medium and its growth dynamics and morphology measured, along with its viability, oxidative stress, mitochondrial function, and autophagy function. In one embodiment, the reference biomarker profile may include data for growth dynamics, morphology, viability, oxidative stress, mitochondrial function, and autophagy function of the healthy sample. This baseline of the reference biomarker profile may be compared to the PD patient's baseline profile (e.g. non-stressed samples).

In other embodiments, the healthy biological sample may also be stress-induced by exposure to the external agent for the period of time. For example, the healthy biological sample is stress-induced along with the PD patient's biological sample, or separately from the PD patient's biological sample. In other embodiments, the stress-induced AMC may undergo similar tests and assays as the PD sample in order to determine the growth dynamics and morphology viability, oxidative stress, mitochondrial function, and autophagy function of the AMC, thereby generating the reference biomarker profile. The stress-induced profile of the reference biomarker profile may be compared to the patient's PD biomarker profile (e.g. stressed samples).

According to some embodiments, the present invention features a method comprising obtaining a non-neuronal biological sample from a subject, growing said biological sample in a medium, exposing said biological sample in the medium to an external agent for a period of time, where said external agent induces stress in said biological sample, and performing tests and assays on said stress-induced biological sample to determine viability, oxidative stress, mitochondrial function, and autophagy function. In some embodiments, the step of performing tests and assays to determine oxidative stress may comprise measuring reactive oxygen species (ROS) levels and mitochondria-specific ROS levels. In other embodiments, the step of performing tests and assays to determine mitochondrial function may comprise analyzing fibroblast mitochondria levels and mitochondria appearance. In one embodiment, the step of performing tests and assays to determine autophagy function may comprise detecting a presence of autophagic vesicles and structures and measuring levels thereof. In one embodiment, the step of performing tests and assays to determine autophagy function may comprise detecting expression of autophagy marker proteins, such as alpha-synuclein, LAMP1, p62, LC3-I, and LC3-II.

According to further embodiments, the method may also comprise measuring dynamics, morphology, viability, as well as oxidative stress and mitochondrial and autophagic function of said biological sample prior to stress-induction. In one embodiment, the step of measuring growth dynamics may comprise measuring cell densities, spatial arrangement, number of adjacent neighbors, and population doubling time. In another embodiment, the step of measuring morphology may comprise measuring cell size, such as cell area, perimeter, and feret diameters, and measuring cell shape, such as eccentricity and form factor. In one embodiment, the step of performing tests and assays to determine oxidative stress may comprise measuring reactive oxygen species (ROS) levels and mitochondria-specific ROS levels. In other embodiments, the step of performing tests and assays to determine mitochondrial function may comprise analyzing fibroblast mitochondria levels and mitochondria appearance. In one embodiment, the step of performing tests and assays to determine autophagy function may comprise detecting a presence of autophagic vesicles and structures and measuring levels thereof. In one embodiment, the step of performing tests and assays to determine autophagy function may comprise detecting expression of autophagy marker proteins, such as alpha-synuclein, LAMP1, p62, LC3-I, and LC3-II.

In accordance with the embodiments of the invention, the biological sample may comprise skin fibroblasts. In other embodiments, the external agent may be ultraviolet (UV) irradiation. In still other embodiments, the period of time ranges from about 3 to 10 days, with about 10 to 30 minutes of exposure per day. For example, the biological sample may be exposed to UV light, such as UVA, for 15-18 minutes a day for a period of 4 days. As another example, the biological sample may be exposed to UVA for 10-20 minutes a day for a period of 5-10 days. In other embodiments, the biological sample may be exposed to UVA for about 10-15 minutes/day, or about 15-20 minutes/day, or about 20-25 minutes/day, or about 25-30 minutes/day, or more than 30 minutes/day. In yet other embodiments, the biological sample may be exposed to UVA for a period of about 3-5 days, or about 5-8 days, or about 8-10 days, more than 10 days.

Consistent with the embodiments herein, the tests and assays performed on the biological sample to measure growth dynamics and morphology and to determine viability, oxidative stress, mitochondrial function, and autophagy function may be known to one of ordinary skill in the art; non-limiting examples of which are described in the following section.

EXAMPLE

The following is a non-limiting example of practicing the present invention. It is to be understood that said example is for illustrative purposes only and in no way limits the present invention. Equivalents or substitutes are within the scope of the invention.

Patient-derived primary dermal fibroblasts provide the advantages of being a primary cell type, which reflects the unique genotype as well as the chronological and epigenetic aging history of donor individuals. As will be described in the following non-limiting example, dermal fibroblasts generated from skin biopsies obtained from persons diagnosed with late-onset sporadic and LRRK2+ Parkinson's disease (PD), and healthy aged-matched control (AMC) individuals were examined, specifically, the morphology, growth dynamics, response to environmental stress, and the mitochondrial and autophagy-related function of these cells.

It was found that fibroblasts derived from PD patients tend to grow in a more organized and streamlined fashion, and have a faster growth rate. Further, PD cells are significantly smaller and rounder than AMC cells. PD fibroblasts show greater loss of viability and significantly increased ROS and autofluorescence levels compared to AMC fibroblasts, upon UVA induced stress. Significantly lowered RCR and Coupling efficiency, along with increased proton leak, and altered mitochondrial levels and appearance, suggest mitochondrial dysfunction in the PD fibroblasts. PD fibroblasts show greater immunocytochemical expression of α-synuclein compared to AMC cells. PD fibroblasts have greater ongoing macroautophagy than AMC cells at steady state. Upon treatment with UVA, PD cells show further activation of macroautophagy as indicated by increased LCII and Lamp1 levels, and number of visualized autophagic vesicles. However, the corresponding changes in p62 also suggest a potential block in autophagic degradation pathway. Overall, PD patient-derived fibroblasts are significantly different from AMC fibroblasts in terms of growth, morphology, mitochondrial and autophagic function, and show a greater susceptibility to environmental stress.

Methods

Fibroblast culture: Primary skin fibroblasts were initially generated from sun-protected skin biopsies (upper inner arm) of sporadic late-onset PD subjects with no significant family history of PD. For control comparisons, fibroblasts were acquired from similar skin biopsies of age-matched, apparently healthy individuals (age-matched controls, AMC). Sample collection was conducted with the necessary patient consent and approval from the University of Arizona Institutional Review Board. Sequencing results indicated the absence of mutations in LRRK2 (Y1699C, R1441C, G2019S, and 12020T) genes in the patient fibroblasts. PCR was conducted and Sanger sequencing was carried out at the University of Arizona Genomics Core on an Applied Biosystems 3730 DNA Analyzer. Fibroblasts from PD subjects carrying a heterozygous G2019S LRRK2 mutation (obtained as described above) and homozygous G2019S LRRK2 mutation were also included in some experiments for comparison.

The fibroblasts were grown in highly standardized conditions using Dulbecco's modified eagle's medium (DMEM) supplemented with 10% Fetal Bovine Serum, 1× Non-Essential Amino Acids and 0.02% Primocin, in 5% $CO_2$ at 37° C. Given that the number of passages can affect cell phenotype and responses, for all experiments in the study, passage numbers used were kept consistent within groups to avoid cell replication related biases. Also, all experiments utilized cells from passage 4 to 14, and cells were used at ~75% confluence. All fibroblast lines were grown in parallel and assessed in at least triplicate for all experiments. A summary of patient data related to the PD and AMC fibroblast lines is provided in Table 1, and a summary of patient data related to LRRK2 is provided in Table 2.

TABLE 1

Clinical Information on study subjects

|  | AMC | PD |
|---|---|---|
| Age (yrs) | 64.2 ± 3.9 | 65 ± 5.05 |
| N (M/F) | 5 (2/3) | 4 (2/2) |
| Time since diagnosis (yrs) | NA | 7.83 ± 3.34 |
| UPDRS (III) score | NA | 8.1 ± 6.45 |
| Daily L-Dopa (mg) | NA | 456 ± 180 |

Values are expressed as mean ± SD.
All PD patients were taking levodopa with adjunctive dopamine agonist therapy.

TABLE 2

Clinical information on LRRK2 subjects

|  | LRRK2 G2019S Het | LRRK2 G2019S Homo |
|---|---|---|
| Age (yrs) | 67 | 72 |
| Sex | M | M |
| Time since diagnosis (yrs) | 3 | 10 |
| UPDRS (III) score | 2 | Not available |
| Daily L-Dopa (mg) | Not available | Not available |

Growth analysis: Cells were assessed when they reached-75% confluence in culture. Two variables were measured during each passage: (1) The duration in days for the cells to reach 75% confluence; and (2) total viable cell count (using 0.4% Trypan blue staining) at 75% confluence. Population doubling was estimated using the formula Doubling time (DT)=T ln 2/ln(Xe/Xb), where T is the incubation time, Xb is the cell number at the beginning of the incubation time, and Xe is the cell number at the end of the incubation time. Images were taken using a Zeiss inverted microscope with phase capability.

Phalloidin staining: Fibroblasts were plated at 40,000 cells/well, in 24-well plates, on poly-d-lysine (0.1 mg/ml) coated glass coverslips and subsequently fixed using 4% paraformaldehyde (PFA) for 20 minutes at room temperature (RT). After washing with 1× Phosphate-buffered saline or PBS, the cells were treated with 0.1% Triton-X-100 for 5 minutes. Then the cells were stained with Alexa Flour 488Phalloidin and treated with 4', 6-diamidino-2-phenylindole, dihydrochloride (DAPI) for nuclear counterstaining.

Morphological analysis: Fibroblasts plated at 40,000 cells/well, on poly-d-lysine coated glass coverslips placed in 24-well plates, were analyzed. Images of phalloidin stained cells were obtained from 10 random fields/sample before processing in CellProfiler software. An analysis pipeline was created to identify nuclei and cell outlines with reference to DAPI and Phalloidin staining. Images were subsequently processed to quantify area, perimeter, maximum and minimum ferret diameters, eccentricity, and form factor. The density of the fibroblast cultures was analyzed similarly via CellProfiler using images from 5 random fields/sample to generate 'Percent Object Neighbors' and 'Number of Adjacent Cells' data.

UVA radiation: UVA exposure was performed using a KW large area light source solar simulator, equipped with a 1000 W Xenon arc lamp power supply and a VIS-IR bandpass blocking filter plus UVB and C blocking filter (output 320-400 nm plus residual 650-800 nm, for UVA). The output was quantified using a dosimeter with a SED033 detector for UVA (range 315-390 nm, peak 365 nm), at a distance of 365 mm from the source. Using a UVB/C blocking filter, the dose at 365 nm from the source is 5.39 µJ $cm^{-2}$ $sec^{-1}$ UVA radiation with a residual UVB dose of 3.16 µJ cm$^{-2}$ sec$^{-1}$. A total of 18 minutes exposure time per day for 4 consecutive days was used to treat the AMC and PD fibroblasts. This treatment regimen is equivalent to 5.82 J/cm$^2$ UVA per day for a total of 4 days (23.76 J/cm$^2$ total UVA dose).

MTT Assay: Fibroblasts were plated into 96-well plates at 10,000 cells/well (6 replicates per line), and the MTT (3-(4,5-dimethylthiazol-2-yl)-2,5-diphenyltetrazolium bromide) assay performed. Briefly, cells were washed with PBS and placed in phenol-free culture medium. They were then treated with 12 mM MTT at 37° C. for 2 hrs. Crystal formation was initiated by removing the MTT solution from each well and adding DMSO after which cultures were incubated at 37° C. for 10 mins. The solution was vigorously mixed to solubilize crystals, and absorbance read on a standard plate reader at 540 nm.

Reactive oxygen species measurements: ROS was analyzed by flow cytometry using 2',7'-dichlorodihydrofluorescein diacetate (DCFH-DA). One hour after the last UVA irradiation, DCFH-DA (5 µg/mL final concentration) was added to the culture medium and cells were incubated for 1 hr at 37° C. and 5% $CO_2$. Subsequently, the cells were harvested via enzymatic trypsinization using TrypLE Express, washed with PBS, and immediately analyzed by flow cytometry (BD FACScanto II at 488 nm excitation, 530 nm emission and CellQuest software). Similarly, to measure the production of mitochondrial superoxide, cells were trypsinized and incubated in 5 µM MitoSOXRed for 10 mins. Next, the cells were washed in PBS and analyzed by flow cytometry (530 nm excitation, 593 nm emission). For both DCF and Mitosox, to avoid direct photo oxidation, cells were loaded with the indicator dye under light exclusion.

Rhodamine 123 assay: Cells were plated on poly-d lysine (0.1 mg/ml) treated glass coverslips placed in 24-well plates at a density of 40,000 cells/well. Then the cells were treated with VectaCell Rhodamine 123 following manufacturer's instructions. Briefly, after washing with PBS, cells were incubated with Rhodamine 123 labeling solution (diluted 1:100 in PBS) for 30 mins at 37° C. Next, the labeling solution was removed, cells rinsed in PBS, and imaged immediately via confocal microscopy. Five random fields per coverslip were assessed and cells with fragmented mitochondria counted in triplicate experiments.

Mitochondrial stress test: Cells were plated in a 96-well Seahorse XF microplate. Each cell line was optimized at a seeding density of 20,000 cells/well, and each consisted of a minimum of 4 wells per experimental run. Cells were incubated at 5% $CO_2$ for 24 hours prior to starting the experiment. Seahorse XF base medium enriched with 8 mM glucose, 5 mM 1-glutamine and 1 mM sodium pyruvate was warmed up to 37° C. with an adjusted pH of 7.35±0.05. All wells were washed with Seahorse medium three times while carefully making sure that the adherent cells weren't detached from the bottom of the wells. The microplate was warmed up for another 60 minutes in a $CO_2$-free incubator before mitochondrial stress test was initiated. Successive administration of 1.0 µM oligomycin, 1.0 µM FCCP and a combination of 1.0 µM rotenone and 1.0 µM antimycin A were mechanically done in the Seahorse XF Flux Analyzer. Respiratory control ratio (RCR), proton leak (PL, also known as state $4_O$ respiration) and coupling efficiency (CE) were calculated from the obtained oxygen consumption rates during the mitochondrial stress test.

Cellular autofluorescence quantification: As described previously, 1 hr after UVA irradiation, cells were harvested by trypsinization, washed and resuspended in PBS. They were immediately analyzed by flow cytometry (excitation 488 nm, emission 530 nm).

Western blotting: For isolating protein, fibroblasts were trypsinized, washed once in PBS, and resuspended in RIPA buffer containing a protease inhibitor cocktail. After 1 hr incubation in RIPA on ice, cells were sonicated and centrifuged at 4° C. for 30 mins at 15,000× g. The supernatant containing the soluble protein was removed, quantified by the Lowry method, and stored at −20° C. To measure LC3 turnover, cells were incubated with 20 mM $NH_4Cl$ and 300 µM leupeptin for 4 hours in regular medium with serum or serum-free conditions before protein samples were collected.

Protein samples from Control and PD fibroblasts were run on a 12% acrylamide gel and transferred to a PVDF membrane. After 1 hr of incubation with blocking solution [0.1M tris buffered saline (TBS) with 1% bovine serum albumin (BSA) and 5% dry milk], primary and secondary antibodies were applied. Specifically, membranes were incubated overnight in primary antibodies targeting LC3 (1:400) and p62 (1:500) diluted in blocking solution with 0.1% Tween-20. The next day, after washing in 0.1M TBS with 0.1% Tween-20, membranes were incubated in appropriate secondary antibodies. In some embodiments, IR Dye 680Rd (Red) or IR Dye 800CW (Green) secondary antibodies at 1:10,000 were used. All membranes were re-probed for β-Actin (1:500) as a loading control. Proteins bands were detected using a Li-CorOdyssey Imager and quantified using Image Studio 2.0 software. The quantitative data obtained was normalized to β-actin.

mCherry-GFP-LC311 flux assay: Fibroblasts were grown on poly-D-lysine (0.1 mg/ml) coated glass coverslips placed in 24-well plates at a density of 20,000 cells/well for 24 hrs. Then, the cells were infected with Ad-mCherry-GFP-LC3 at multiplicity of infection (MOI) of 10. After 24 hrs post infection, the cells were washed with medium, kept in culture for another 48 hrs, and finally fixed in 4% PFA for confocal imaging. The number of red and yellow puncta/cell and percent area/cell covered by puncta in each cell line was enumerated using a 40× lens in seven random fields in triplicate experiments.

Electron Microscopy: Fibroblasts were plated at 1×10$^6$ cells in a 10 mm petri dish. The cells were subsequently fixed in-situ with 2.5% glutaraldehyde in 0.1M piperazine-N,N'-bis (2-ethanesulfonic acid) or PIPES buffer for 30 mins at room temperature, and washed with 0.1M PIPES/Glycine buffer for 10 mins and PIPES for 5 mins. Subsequently, the cells were post-fixed with 1% osmium tetroxide in PIPES for 30 mins, washed in distilled/deionized water (DIW), scraped off well bottoms, and transferred to 2 ml microfuge tubes in which they were pelleted. Cell pellets were further washed with DIW, re-pelleted, stained with 2% uranyl acetate for 20 mins and washed again in DIW. Pellets were dehydrated through an ethyl alcohol series and acetonitrile and infiltrated with 50/50 acetonitrile/Embed 812 resin overnight. Following further infiltration with 100% resin (3×60 mins) pellets were allowed to polymerize in the microfuge tubes overnight at 60° C. Sections of 70 nm sections were cut on a Leica Ultracut UCT ultramicrotome onto uncoated 150 mesh copper grids and counter-stained with lead citrate. Sections were viewed in an FEI TecnaiBiotwin electron microscope operated at 100 kv. Eight bit TIFF images were collected via a 4 MP XR41 AMT side-mount camera. Morphometric measurements were conducted in digital images using Image J software. The number of autophagic vacuoles per cell profile (16-18 cell profiles) in triplicate experiments was counted.

Alpha Synuclein Immunocytochemistry and Quantification. Fibroblasts were plated at 20,000 cells/well on poly-d-lysine coated glass coverslips placed in 24-well plates. Subsequently, cells were fixed in 4% paraformaldehyde, and treated with primary antibodies targeting alpha synuclein (1:100) followed by appropriate secondary antibodies and tags (goat anti-mouse biotin (1:400) and Streptavidin 555 (1:100)). Cells were then counterstained with the nuclear stain DAPI. Immunostained slides were analyzed using a Zeiss Axiolmager M2 microscope (Zeiss, Jenna, Germany) with an AxioCam MRm camera and associated Axiovision software (version: Axio Vision Rel.4.8.2; Zeiss) using a 20× lens. Five random fields were imaged per stained sample, with 3 such samples being analyzed for each cell line. The intensity of alpha synuclein was measured via a plate reader and presented in the graphs as mean SEM.

Microscopy: A Zeiss Axiolmager A1 inverted microscope with phase capability, with an AxioCamMRc camera and associated AxioVision software, was used to qualitatively analyze the fibroblasts in culture. Fluorescence analysis was performed using a Zeiss M2 Imager microscope connected to an AxioCamMRm digital camera or Leica DM16000 inverted fluorescence microscope equipped with Suite-Advanced Fluorescence 3.0 Leica Application. A Leica SP5-11 confocal microscope was used for the mitochondrial Rhodamine 123 and LC311-mcherry-GFP assays. Z sectioning was performed at 1-2 μm intervals in order to verify the co-localization of markers. Image extraction and analysis was conducted via the Leica LAS software.

Statistical Analysis: All statistical analyses were performed using GraphPad Prism 6.0 software. For normally distributed data, for comparing two groups, analysis was conducted via unpaired t-tests with Welch's correction. For non-normally distributed data, medians were calculated and non-parametric testing was conducting using a Mann Whitney U-test. For comparisons between three or more groups, analysis of variance (ANOVA) followed by Bonferroni's post hoc test for multiple comparisons between groups was conducted. All data are presented as mean±SEM, except in FIG. 5J which depicts median±interquartile range. A $p \leq 0.05$ was considered as significant in all cases.

Results

Figure 2A:
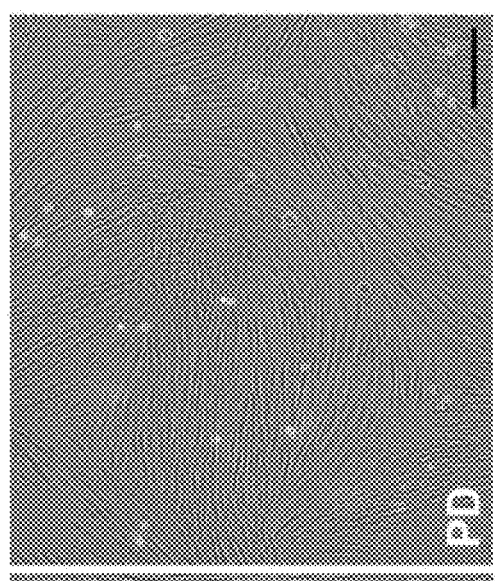
Figure 2B:
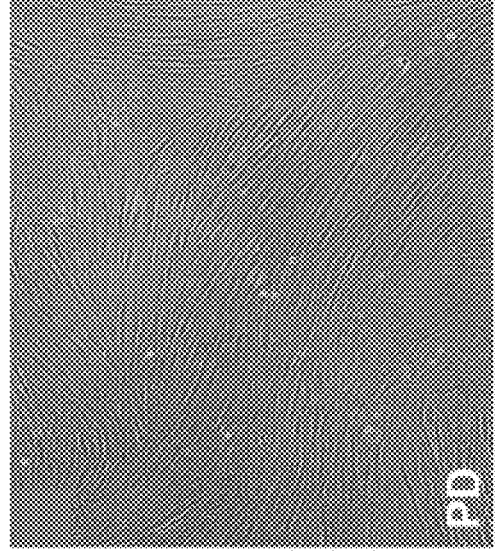
Figure 2C:
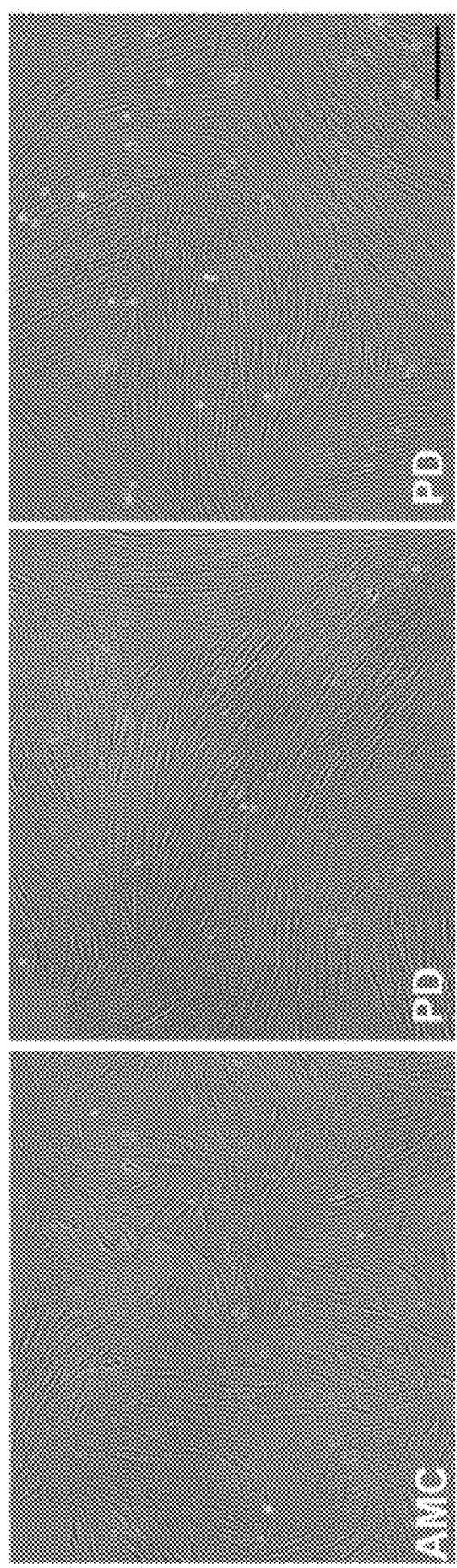
Figure 2D:
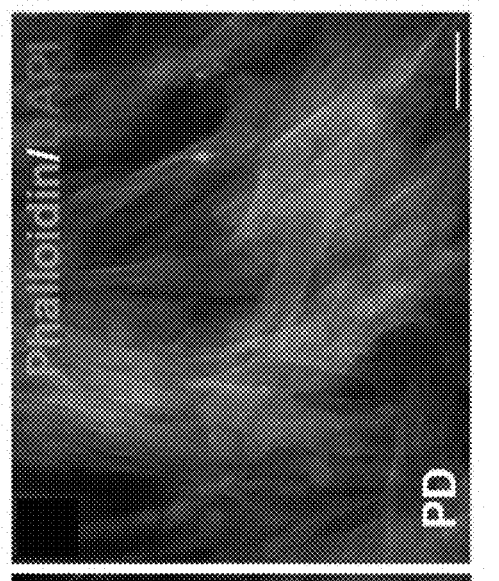
Figure 2E:
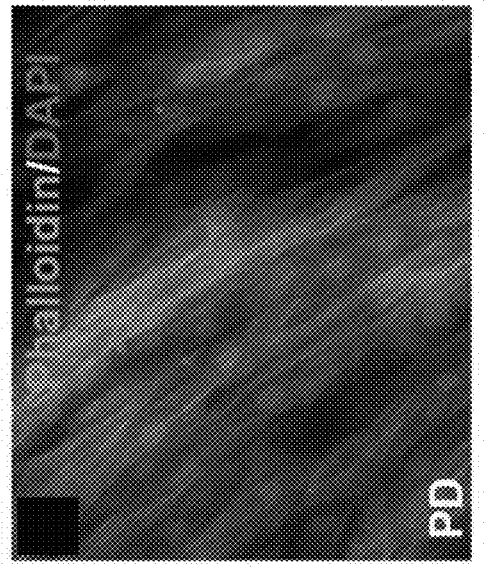
Figure 2F:
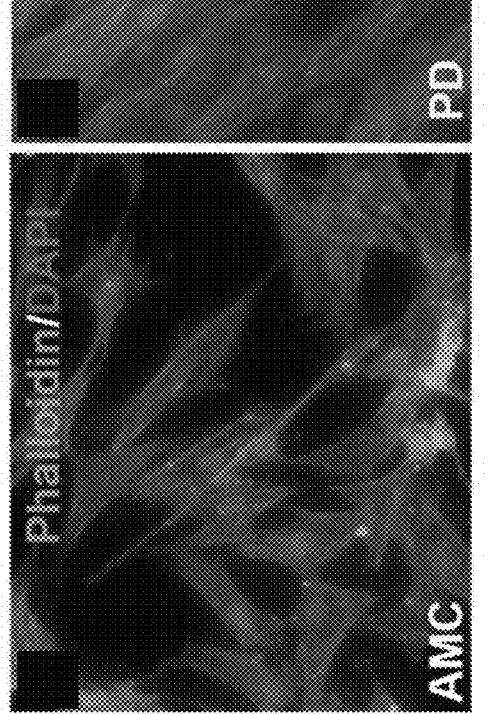
Figure 9A:
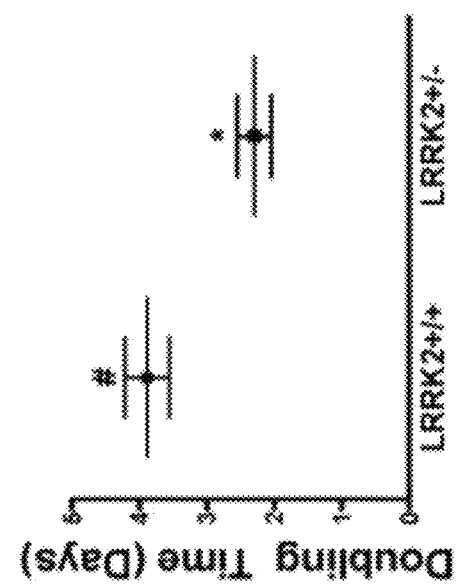
FIGS. 9A-9J show LRRK2 mutated fibroblasts having specific alterations in growth and morphology. Qualitative representations of LRRK2+/+ and LRRK2+/− cultures in phase and after Phalloidin staining are shown in FIGS. 9A-9B and 9D-9E. LRRK2+/+ cells showed higher doubling times and lower number of cellular neighbors touching compared to sporadic PD and LRRK2+/− cells (FIGS. 9C, 9F). The LRRK2 cells were larger (FIGS. 9G, 9H), less eccentric and more ramified compared to other PD cells (FIGS. 9I, 9J). Scale Bars.
Figure 9B:
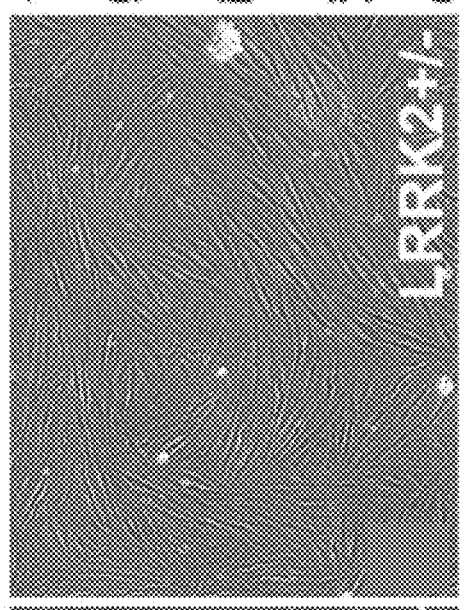

PD Skin Fibroblasts Show Distinct Alterations in Growth Rate and Spatial Arrangement in Culture First, the growth characteristics of fibroblasts obtained from PD and AMC individuals were studied. It was observed that while AMC cultures exhibited features typical of mature fibroblasts, PD cultures appeared distinctly different (FIGS. 2A-2C show phase contrast images; FIGS. 2D-2F show fluorescent images of Phalloidin/DAPI stained cells). More specifically, while AMC cells were larger, more evenly distributed, and displayed a ramified (several processes) structure, PD cells were noted to be smaller, more spindle shaped, and grouped together in a 'stream-like' fashion along their longitudinal axis. Additionally, PD cultures showed higher cell densities compares to AMC cultures. These specific differences in growth and morphology between the PD and AMC cells were consistently observed across several passages in culture. Furthermore, these cell lines were also compared to PD cells with a G2019S LRRK2 homozygous (LRRK2+/+) mutation (positive control). It was observed that the LRRK2+/+ cells grew unevenly in concentrated groups in culture (FIGS. 9A, 9D). On the other hand, cells with heterozygous G2019S (LRRK2+/−) mutation appeared qualitatively similar to sporadic PD cells (FIGS. 9B, 9E).

Figure 2G:
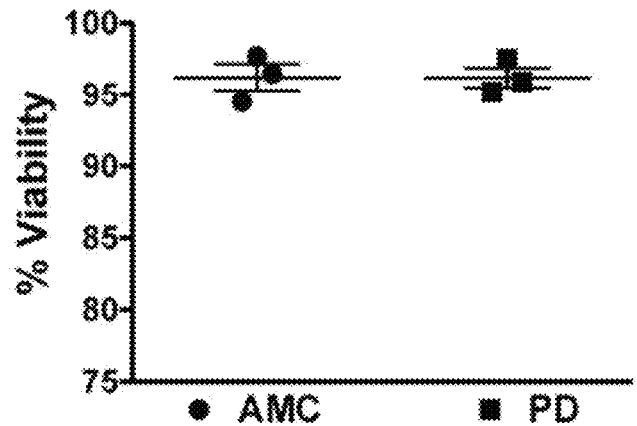
Figure 2H:
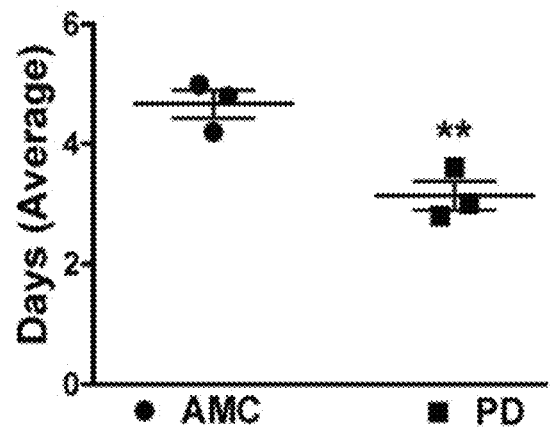
Figure 2I:
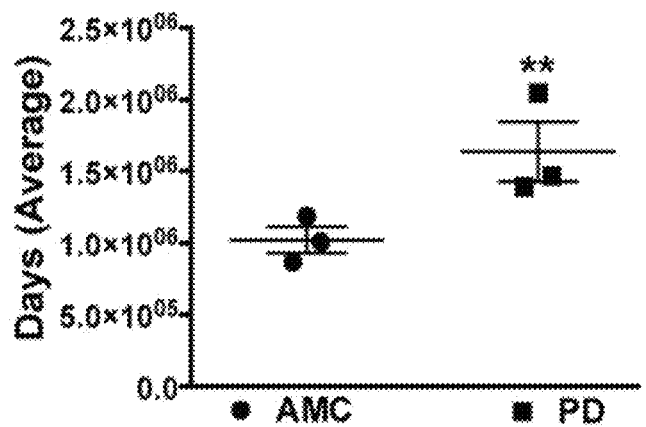
Figure 2J:
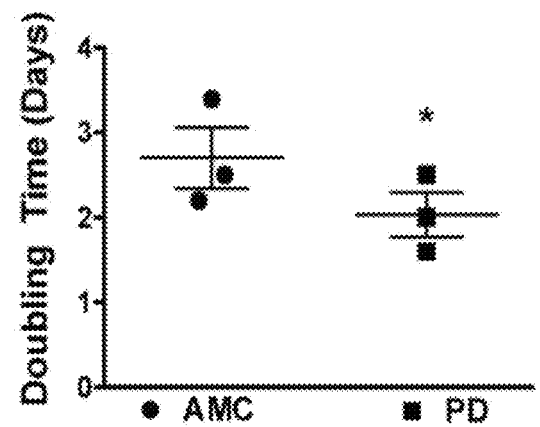

The viability of the fibroblasts was examined using a Trypan blue assay at a stage right before passage when they had reached ~75% confluence. The results indicated that cell viability did not differ significantly between PD and AMC fibroblast lines (FIG. 2G; p>0.05, t=0.022, df=15.59, Unpaired t-test). However, when the number of days taken to reach 75% confluence was quantified, this measure was noted to be customary (4-5 days) of growing fibroblasts in the AMC cells, but was significantly lower (2-3 days) in the PD cultures (FIG. 2H; p<0.01, Unpaired t-test). Moreover, when the total number of cells in the culture flasks was enumerated at 75% confluency, it was found that there were significantly higher numbers of cells in the PD flasks (FIG. 2I; p<0.01, Unpaired t-test). In fact, although all flasks were seeded initially with 350,000 cells during passage, the PD cells multiplied to an average of ~$1.7 \times 10^6$ cells/flask, compared to AMC cells which reached only $1 \times 10^6$, at the 75% confluence stage. Additional analysis indicated that the population doubling time (DT) of AMC fibroblasts was significantly greater at 3.02±0.33 compared to a shorter 2.1±0.3 in PD cells (FIG. 2J; p<0.05, Unpaired t-test).

Figure 9C:
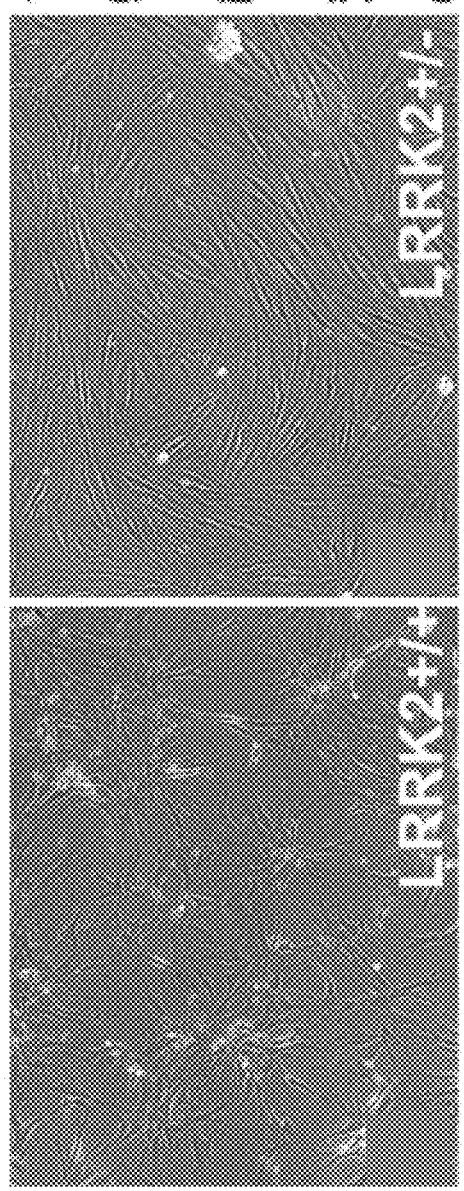
Figure 9D:
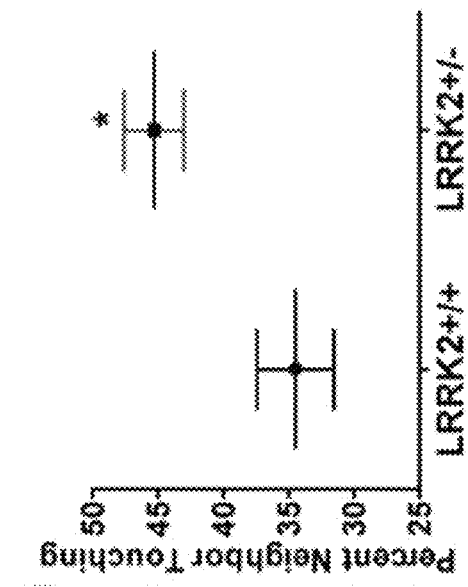
Figure 9E:
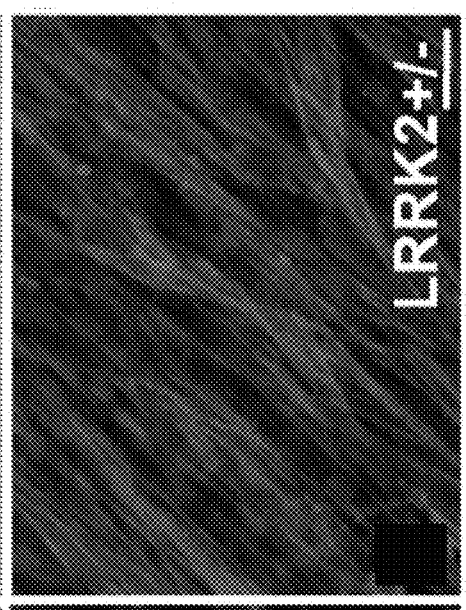

Comparatively, the DT of LRRK2+/+ cells was significantly higher (p<0.05) than sporadic PD and LRRK2+/− cells (FIG. 9C, Unpaired t-test).

Figure 2K:
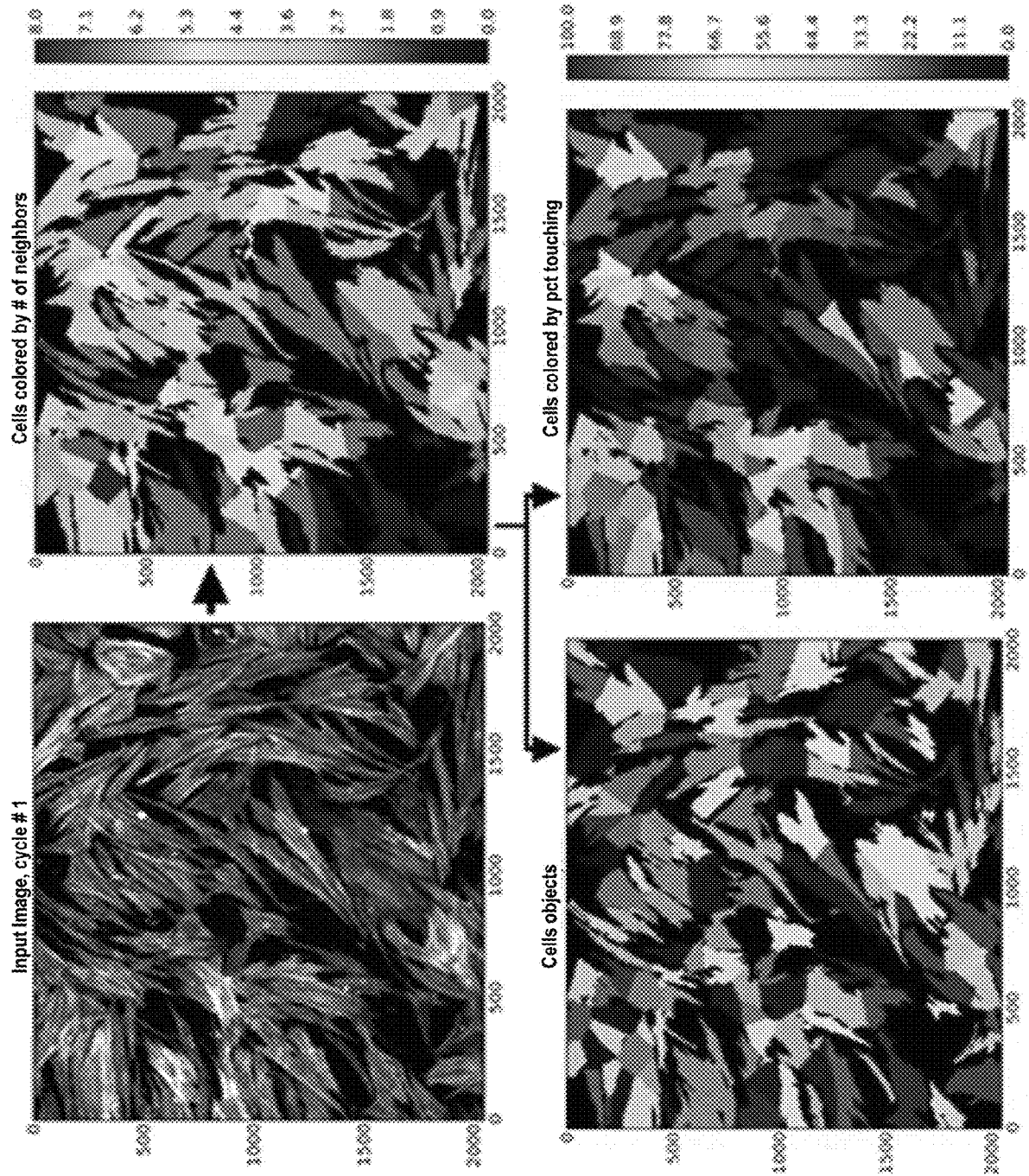
Figure 9F:
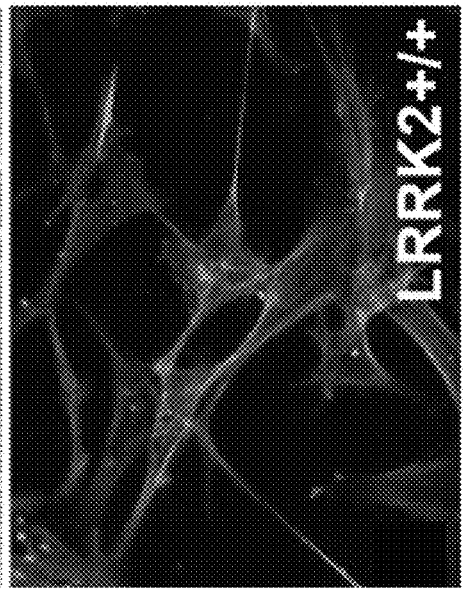
Figure 9G:
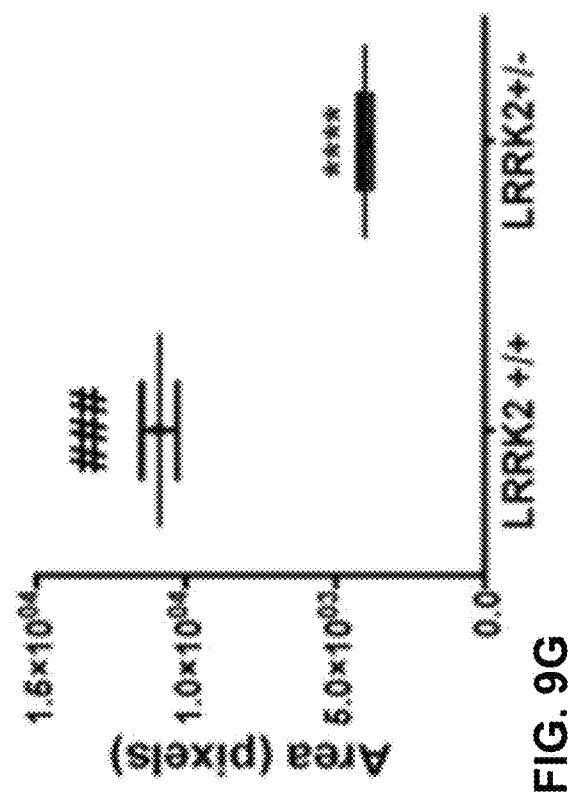
Figure 9H:
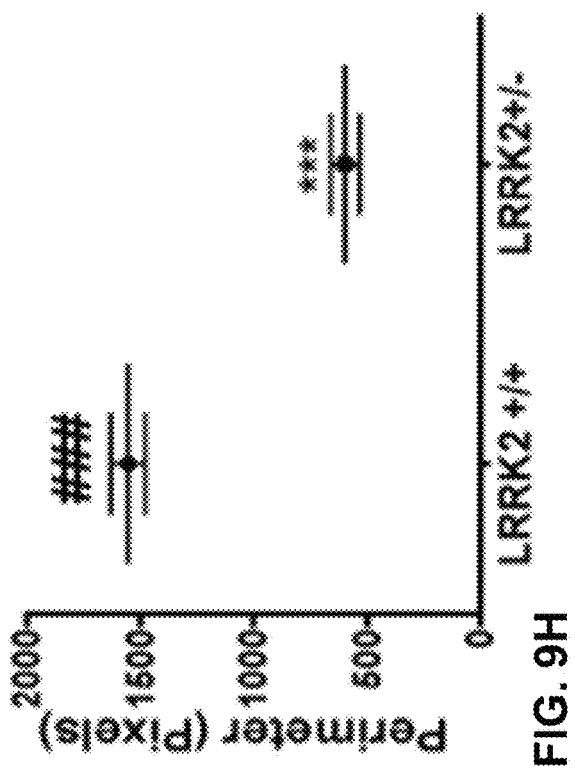
Figure 9I:
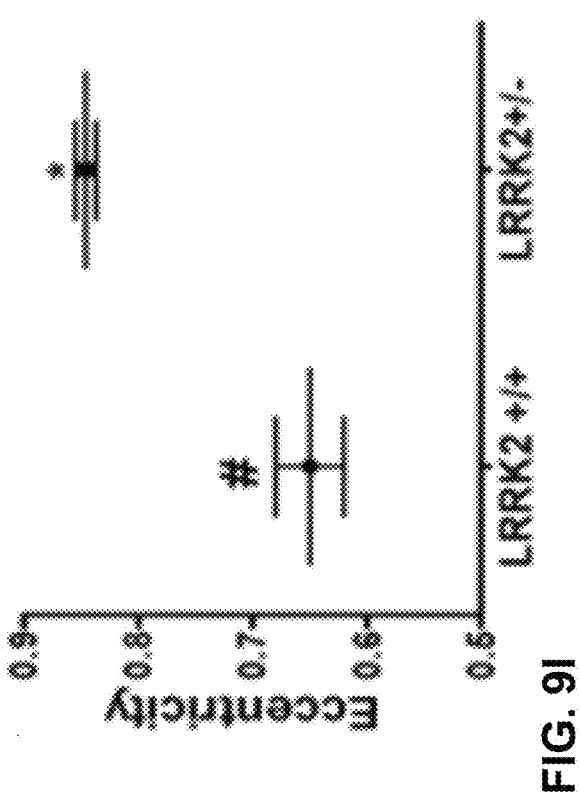
Figure 9J:
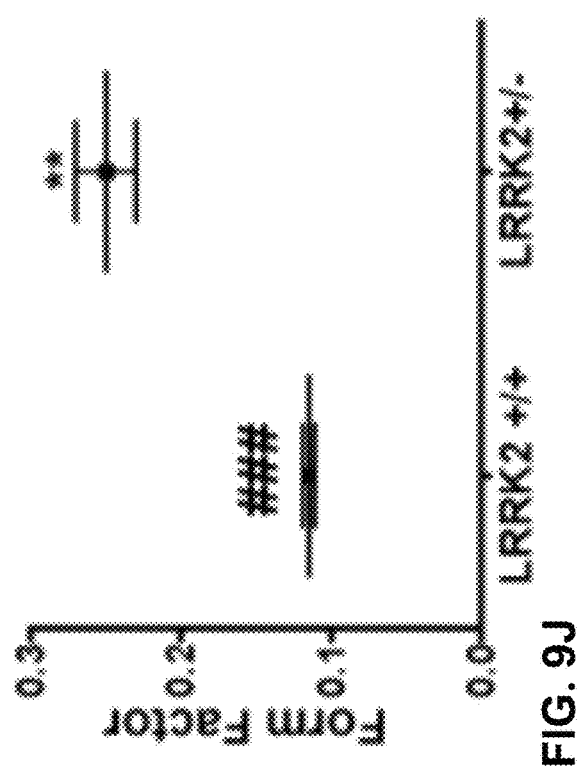

Additionally, the density and spatial arrangement of the cells at the 75% confluence stage were analyzed. Mainly, using the image analysis software CellProfiler, on Phalloidin/DAPI stained cells, the number of adjacent neighbors that each cell in culture had was quantified (FIG. 2K), as well as the number of neighboring cells, which were in contact, or overlapping, with each other. These data showed that cells in PD flasks had about 45% of neighbors touching compared to AMC flasks where only about 20% of cells had neighbors touching (FIG. 2L, p<0.0001, Unpaired t-test). Similarly, it was found that PD fibroblasts had a higher number of adjacent neighbors compared to AMC fibroblasts (FIG. 2M; p<0.01; Unpaired t-test). Overall, these data determined that PD cultures were denser and contained more closely affiliated cells than AMC cultures. The LRRK2+/+ cultures in contrast had significantly (p<0.01. Unpaired t-test) lower percentage of neighboring cells in contact with each other compared to sporadic PD and LRRK2+/− cells (FIG. 9F).

Figure 3B:
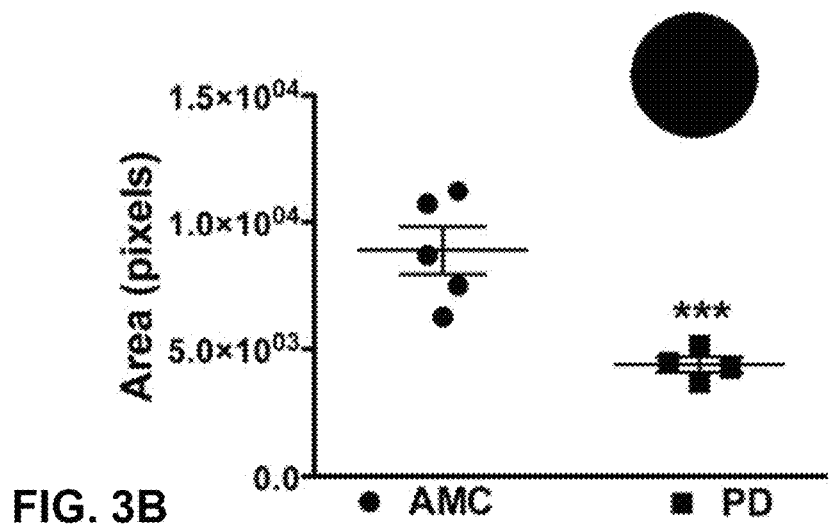
Figure 3C:
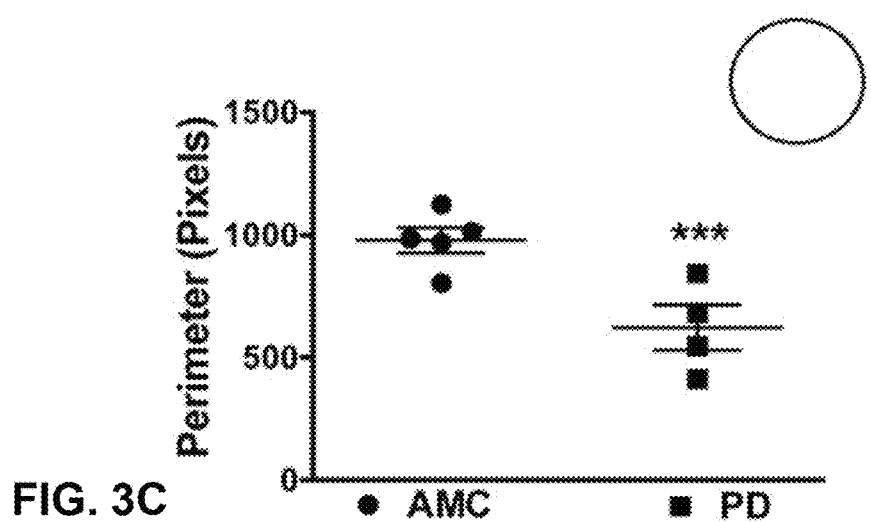
Figure 3D:
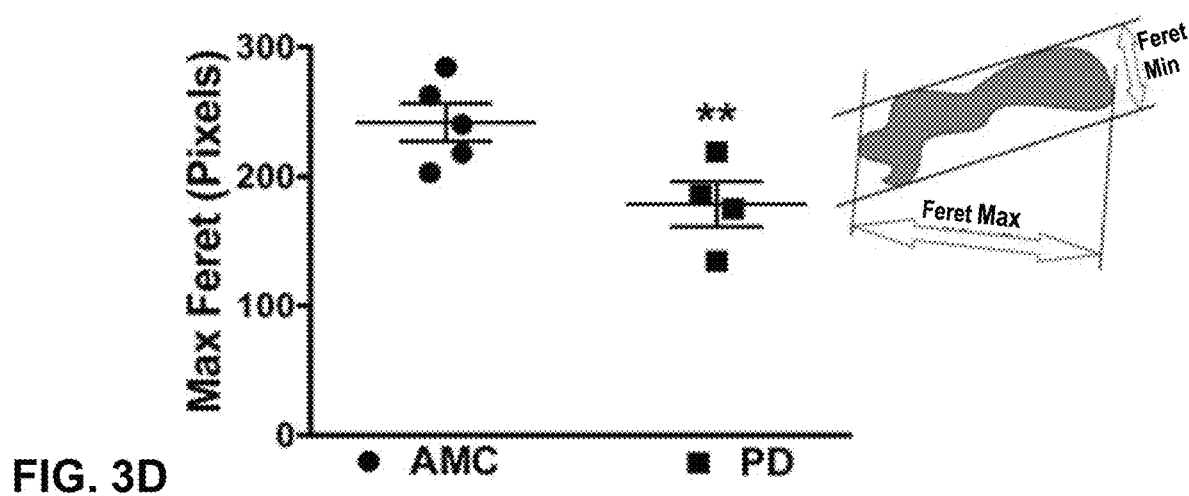
Figure 3E:
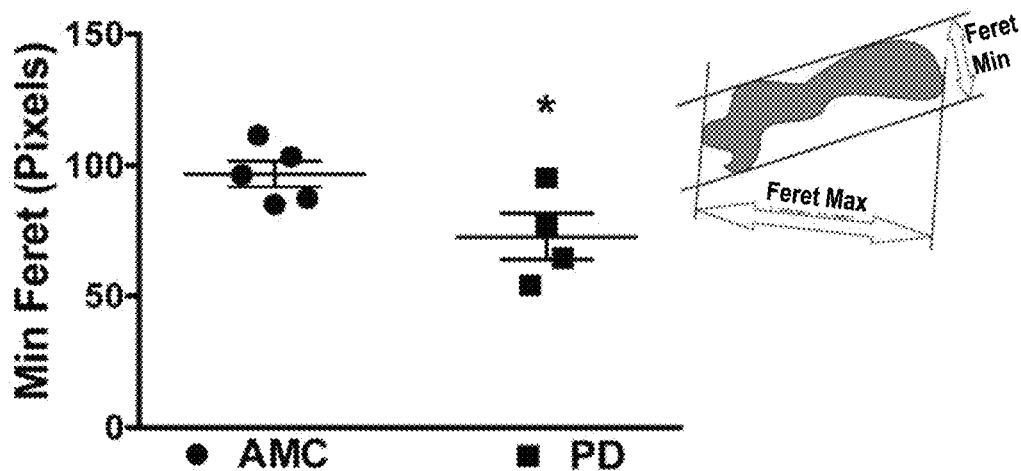
Figure 3F:
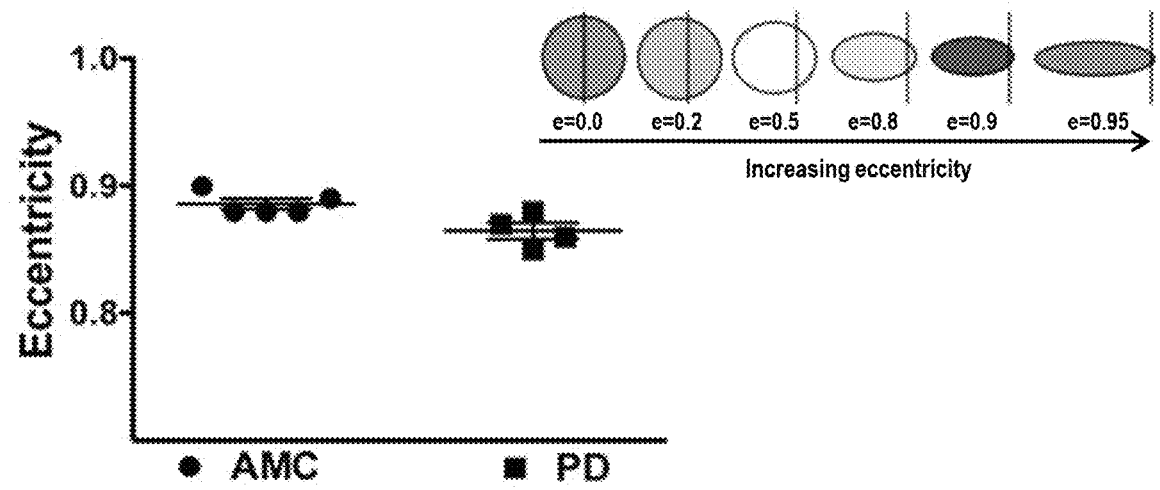
Figure 3G:
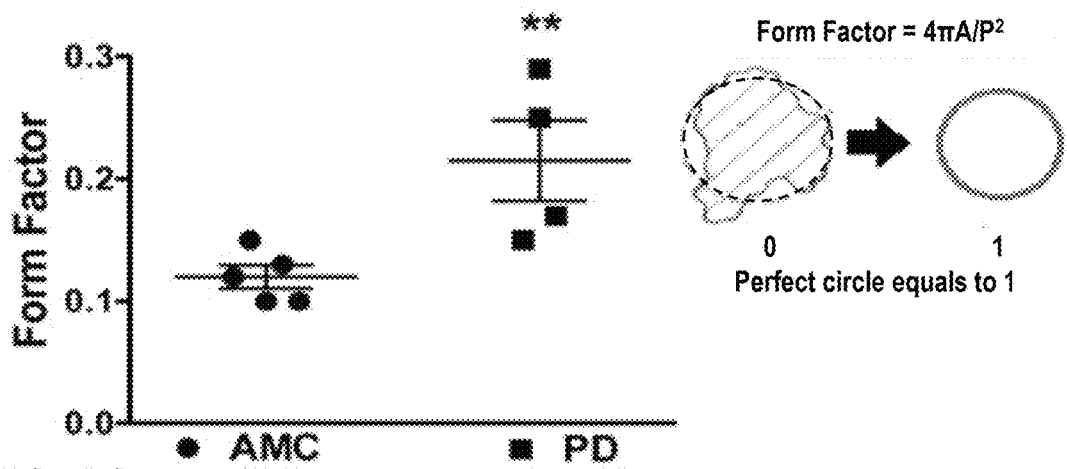

PD-Patient Derived Skin Fibroblasts are Morphologically Different than Those from Healthy Controls The morphology of the patient-derived fibroblasts was also examined. Specifically, the fibroblasts were stained with Phalloidin and DAPI to allow clear demarcations of cell size and shape, after which they were analyzed via the CellProfiler software (FIG. 3A). Cell size, area, perimeter, and maximum and minimum feret diameters (major and minor axis of the cell) were calculated. It was found that, on average, PD cells had significantly lower area (FIG. 3B; p<0.001, Unpaired t-test), perimeter (FIG. 3C; p<0.001, Unpaired t-test), and feret diameters (FIG. 3D: p<0.05, Unpaired t-test; FIG. 3E: p<0.05, Unpaired t-test), indicating that they were smaller compared to control cells. With regards to shape, the eccentricity (a measure of cell elongation) and form factor (a measure of roundness) of the fibroblasts were measured. It was noted that although both PD and control cells were both elongated in shape (FIG. 3F), PD cells were significantly more defined (that is less ramified) than AMC fibroblasts (FIG. 3G; p<0.01, Unpaired t-test).

Interestingly, it was determined that the LRRK2+/+ fibroblasts were significantly ($p<0.001$, Unpaired t-test) smaller (lower area and perimeter), and less defined (reduced form factor, $p<0.001$, Unpaired t-test) compared to sporadic PD fibroblasts. They were also significantly ($p<0.05$, Unpaired t-test) less elongated compared to both PD and AMC cells (FIGS. 9G-9J). These data altogether supported the qualitative observations (FIGS. 2A-2F, FIGS. 9A, 9B, 9D, 9E) demonstrating that the morphology of PD fibroblasts was indeed different than AMC fibroblasts.

Figure 4H:
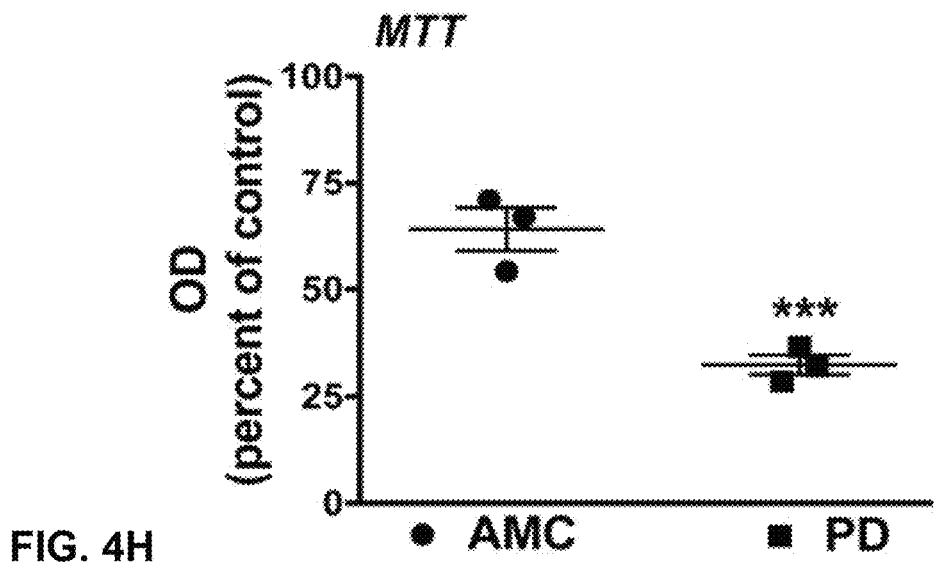
Figure 10E:
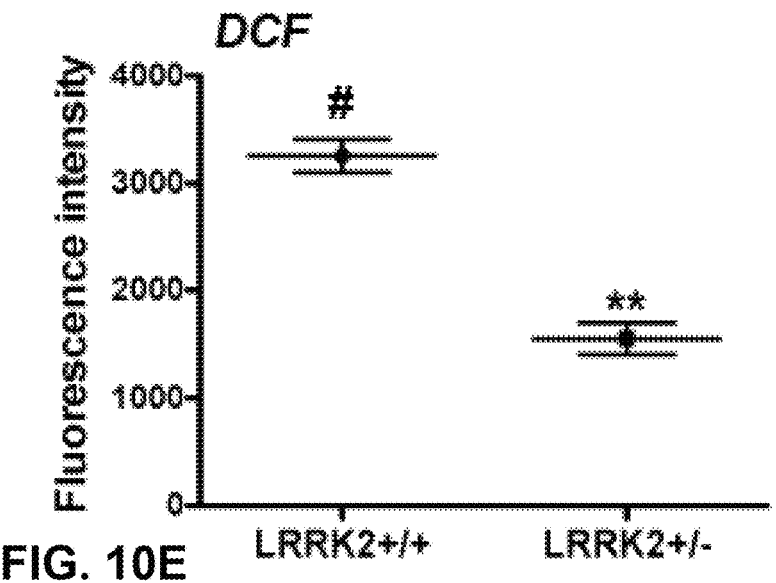

PD Skin Fibroblasts Show an Increased Susceptibility to Oxidative Stress after UVA Exposure The patient fibroblasts were also exposed to ultraviolet (UV) irradiation, an environmentally relevant stressor. Specifically the cells were treated with UVA, which is the more deeply penetrant type of solar UV radiation and constitutes most of the UV energy to which human skin is exposed (>95%, 320-400 nm) (FIG. 4A). UVA is also an inducer of oxidative stress and skin photo aging. A subchronic UVA regimen that delivered a physiologically appropriate dose was applied, without overt cell loss in AMC cells. Subsequently, the viability and production of reactive oxygen species (ROS) in the AMC and PD fibroblasts was measured. Firstly, it was found that under baseline conditions, although there were no statistically significant differences in viability (MTT cytotoxicity assay, FIG. 4B), the differences in total cellular ROS levels (indicated by DCFH-DA fluorescence which represents peroxide species levels, FIG. 4C) were almost statistically significant ($p=0.056$) between the AMC and PD cultures. In contrast, DCFH-DA fluorescence in LRRK2+/+ cultures was significantly ($p<0.05$, Unpaired t-test) higher than AMC or LRRK2+/− cultures (FIG. 10E).

Figure 4I:
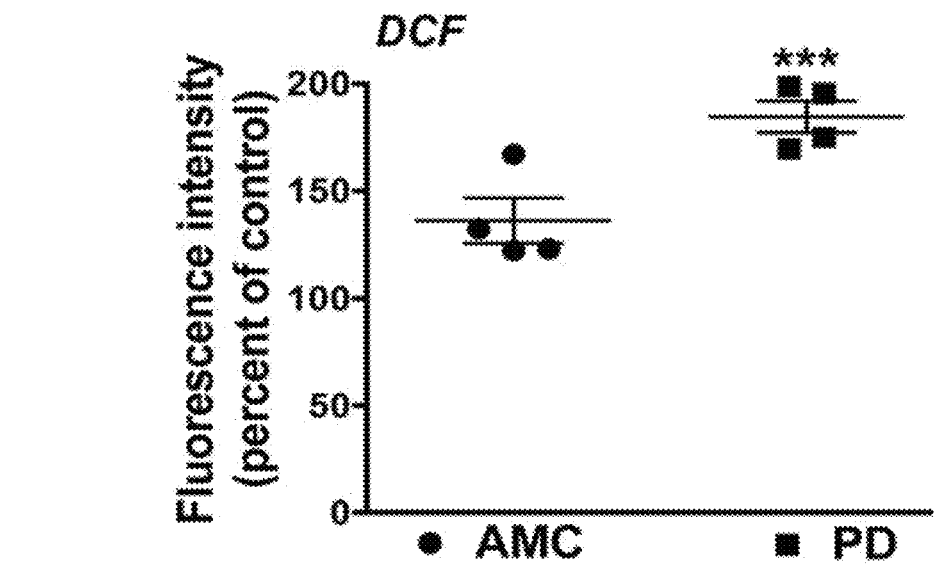
Figure 4J:
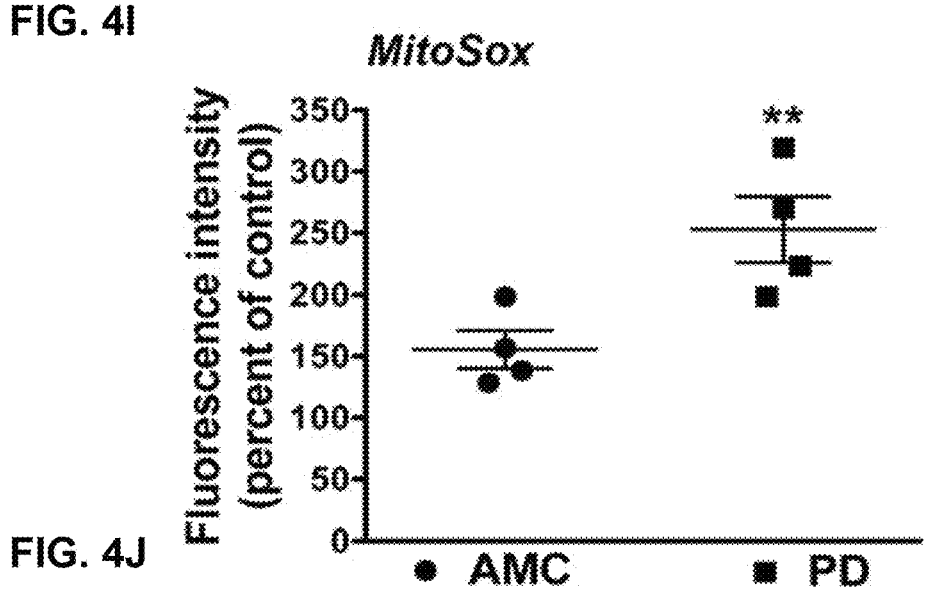

Upon UVA treatment, it was noted that although there was some cell loss and shrinkage occurring in AMC cultures, a drastic reduction in cell survival was seen in the sporadic PD cells (FIGS. 4D-4G). Further analysis via the MTT assay (FIG. 4H) showed that PD cells had indeed undergone a significantly greater decline in viability (~77%), in comparison with control cells (~26%). Moreover, flow cytometric analysis of oxidative stress showed greater shifts in ROS fluorescence intensity peaks suggesting higher UVA induced ROS production in PD cells. More specifically, PD cells exhibited significantly higher total cellular ROS (DCFH-DA fluorescence, FIG. 4I) as well as mitochondria-specific ROS (indicated by Mitosox fluorescence measurements, FIG. 4J). In fact, total ROS in PD cells increased to about 181%, compared to 131% in AMC cells (FIG. 4J; $p<0.001$, One-way ANOVA). The changes in mitochondrial ROS production were even more pronounced, and showed an increase to 247% in PD cells compared to 155% in AMC cells (FIG. 4J; $p<0.01$, One-way ANOVA). Overall, these data indicated that PD cells had higher baseline ROS, and were substantially more sensitive to UVA-induced oxidative stress than AMC cells.

Mitochondrial Function is Impaired in PD Skin Fibroblasts

Figure 10F:
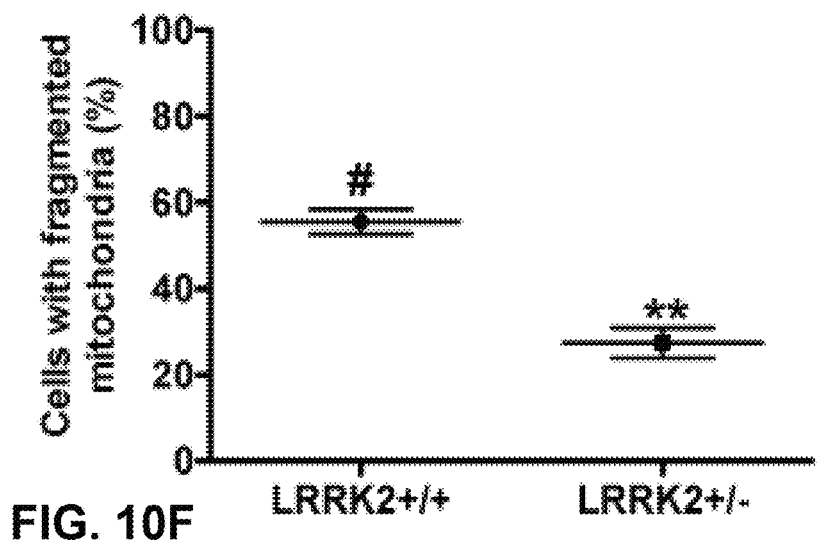

Given the significantly higher mitochondrial ROS production noted in PD cells after UVA stress, the mitochondrial morphology and function of the patient fibroblasts was further examined. To examine morphology, fibroblast mitochondria was labeled with Rhodamine 123, a cationic fluorescent dye that labels respiring mitochondria. The dye distributes according to the negative membrane potential across the mitochondrial inner membrane. Loss of mitochondrial membrane potential results in reduced fluorescence intensity. In these experiments, it was observed that mitochondria in AMC fibroblasts had higher Rhodamine 123 fluorescence (FIG. 5A). In addition, the AMC mitochondria showed normal morphology, with typical size and tubular network structure (FIG. 5B, confocal maximum intensity projection image). On the other hand, mitochondria in PD fibroblasts exhibited lower Rhodamine 123 fluorescence and a fragmented appearance indicating impaired mitochondrial functioning (FIGS. 5C-5D, confocal maximum intensity projection image). Quantitative analysis indicated that PD fibroblasts had significantly more cells with fragmented mitochondria than control fibroblasts (FIG. 5E, $p<0.05$, Unpaired t-test). Moreover, the LRRK2+/+PD fibroblasts also showed lower Rhodamine 123 fluorescence (several cells showed virtually no Rh123 fluorescence retention in mitochondria (FIG. 10A; arrows) and significantly ($p<0.05$, Unpaired t-test) higher numbers of fragmented mitochondria (FIG. 10F) compared to sporadic PD and LRRK2+/− cells.

Figure 10G:
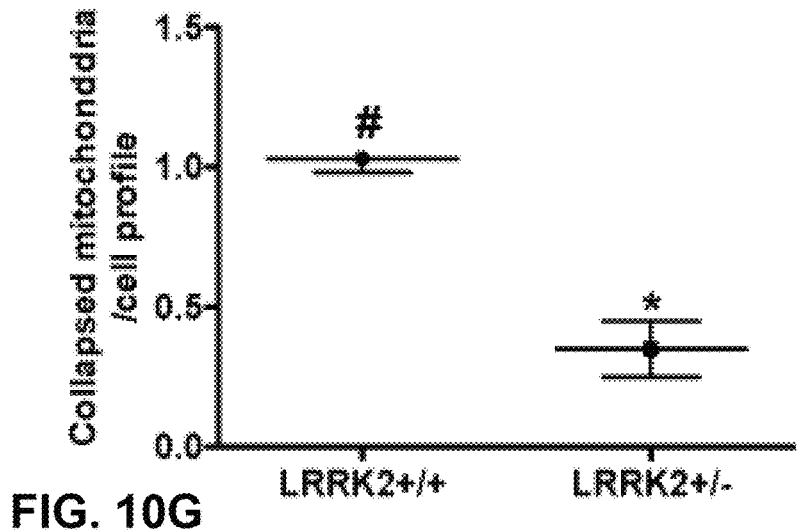

Additional morphological examination via electron microscopy also supported a role for mitochondrial dysfunction in the PD fibroblasts. Here, it was observed that while AMC cells showed normal mitochondrial ultrastructure, with expected shape, size, and intact cristae (FIG. 5F), mitochondria in PD fibroblasts exhibited several alterations. Specifically, smaller mitochondria lacking typical cristae (FIG. 5G), as well as a number of mitochondria undergoing autophagy (enclosed within autophagic vesicles, FIG. 5H) were seen in PD cells indicating ongoing 'mitophagy' of subpar mitochondria. Also, mitochondria which had lost their tubular shape and appeared collapsed were predominantly noted in the PD cells (FIG. 5I, J, $p<0.0001$, non-parametric Mann Whitney U-test). The LRRK2+/+ cells also showed significantly more ($p<0.05$, Unpaired t-test) collapsed mitochondria compared to sporadic PD and LRRK2+/− cells (FIGS. 10C, 10D, 10G).

Given the morphological mitochondrial changes observed, mitochondrial function was further assessed by measuring oxidative phosphorylation (OXPHOS) activity using the Seahorse MitoStresstest (FIG. 5K). Three important parameters, namely respiratory control ratio (RCR), proton leak (PL), and coupling efficiency (CE), were assessed. The data indicated that the PD cells, on average, had significantly lower RCR (FIG. 5L; $p<0.05$; two-way ANOVA), which is the ratio between maximal uncoupled oxygen consumption (with the administration of FCCP) and state $4_O$ OCR (or proton leak). In concert with the RCR findings, proton leak (PL) was determined to be higher in PD fibroblasts compared to AMC cells (FIG. 5M; $p<0.05$; two-way ANOVA). Furthermore, the PD fibroblasts were found to have a lower coupling efficiency, suggesting that the increased PL may be the cause of lowered ATP reserve in PD cells (FIG. 5N; $p<0.05$; two-way ANOVA). Taken together, these data supported the presence of a baseline mitochondrial dysfunction in PD fibroblasts.

PD Skin Fibroblasts Display Altered Baseline Levels of Autophagy

Next, the fibroblasts were examined via electron microscopy for evidence of autophagy, specifically macroautophagy. It was seen that while AMC cells showed the presence of some autophagic vesicles (FIGS. 6A-6B; black arrows), sporadic PD fibroblasts exhibited a significantly increased collection of autophagic structures in their cytoplasm (FIG. 6C, black arrows). A striking accumulation of autophagic vesicles (FIG. 6F, $p<0.01$, Unpaired t-test) was observed in sporadic PD cells, with both typical double membrane bound autophagosomes (FIG. 6D; black arrowhead), as well as autolysosomes (FIG. 6E; white arrowhead). The LRRK2+/+ cells showed the greatest changes and displayed significantly higher numbers of autophagic vesicles than AMC, sporadic PD and LRRK+/− fibroblasts (FIGS. 11A-11C).

To further investigate the electron microscopic findings, the macroautophagy pathway was examined by looking at the expression of two standard autophagy markers, specifically LC3 and p62, in the fibroblasts using western blotting. LC3 is involved in autophagosome formation/maturation and p62 is involved in 'guiding' ubiquitinated cargo for degradation. These experiments showed that LC3 levels were significantly lower in the PD fibroblast lines as compared to AMC lines (FIGS. 6G, 6I). To understand whether the decrease in LC3 11 was due to the reduced production or increased degradation of LC3 11, the cells were treated with a combination of ammonium chloride and leupeptin (lysosomal inhibitors) to measure autophagic flux. Upon this treatment, an increased accumulation of LC3 11 was noted in PD cells (FIGS. 6H, 6J) indicating higher LC3 11 degradation/turnover. When levels of p62 were analyzed, PD cell lines showed lower p62 expression compared to AMC lines, further supporting the notion that indeed autophagic degradation was greater in the PD cells (FIGS. 6K, 6M). This was additionally confirmed when increased p62 was noted in PD cells (FIGS. 6L, 6N) upon exposure to ammonium chloride and leupeptin. All in all, these data supported the presence of higher basal autophagy in PD fibroblasts.

The autophagy flux was further monitored in the fibroblasts through direct fluorescence microscopy by applying aviral mCherry-GFP-LC3 tandem construct. Upon transfection of this construct, it was noted that very few autophagosomes (yellow puncta) and autophagolysosomes (red puncta) were present in AMC cells (FIGS. 6O-6R). However, substantially more autophagosomes, and autophagolysosomes, were noted in PD cells suggesting again a greater autophagic flux (FIGS. 6S-6V). Quantitative data showed that the total area covered by puncta, as well as average number of puncta, were greater in PD cells compared to AMC cells (FIG. 6W, p<0.05, Unpaired t-test; FIG. 6X, p<0.05, Unpaired t-test). The percentage of autophagosomes and autolysosomes were found to be comparable in the PD cells, thus indicating greater flux (FIG. 6Y). In summary, these data together indicated an up-regulation of baseline autophagic activity in the PD fibroblasts.

Alpha-Synuclein Analysis

Immunocytochemical staining (FIGS. 7A-7B) and Cell-Profiler quantification (FIG. 7C) showed that fibroblasts from Parkinson's patients had higher expression of the PD-relevant protein alpha-synuclein (α-synuclein) than AMC fibroblasts.

UVA Promotes Autophagic Dysfunction in the PD Skin Fibroblasts

Figure 8A:
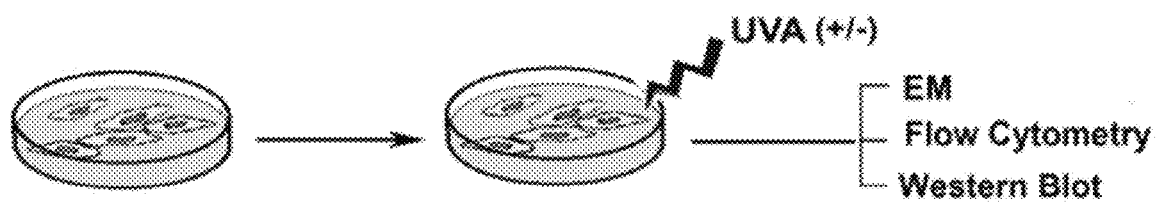
Figure 8B:
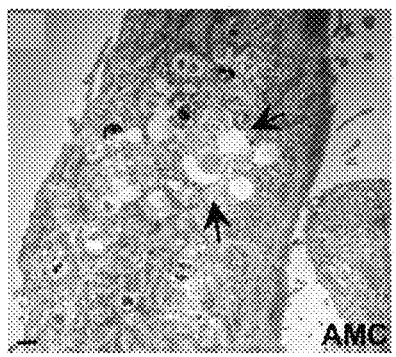
Figure 8C:
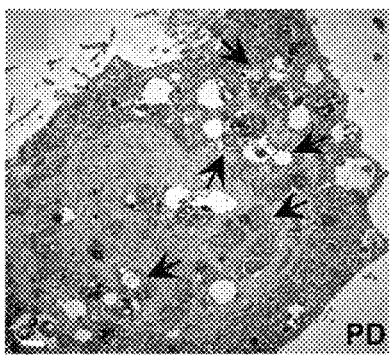
Figure 8D:
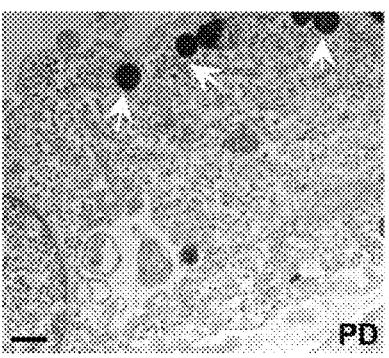
Figure 8E:
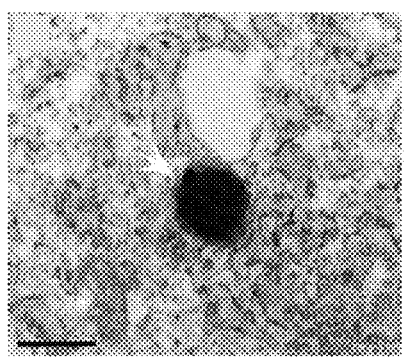
Figure 8F:
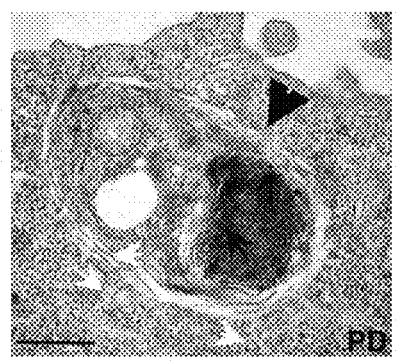

Autophagy after exposure to subchronic UVA treatment, which can cause autophagic-lysosomal blockade in human dermal fibroblasts, was assessed (FIG. 8A). Electron microscopic analysis showed an increased presence of autophagic vesicles in the AMC fibroblasts upon UVA exposure (FIG. 8B; black arrows). However, an even greater autophagic response was noted in PD cells, where a widespread and exaggerated collection of autophagic structures was seen (FIGS. 8C-8F; arrows). Quantitative analysis confirmed the significantly increased presence of autophagic structures in PD cells (FIG. 8G; p<0.01, Unpaired t-test). Furthermore, in addition to typical autophagosomes and autophagolysosomes (FIGS. 8C, 6F; black arrows, black arrowhead showing high magnification of an autophagolysosome), a marked increase in very dense structures, potentially compatible with lysosomes containing undegraded residues, was seen broadly in PD cells (FIG. 8D, 8E, 8I; white arrows). Given the autofluorescent nature of lipofuscin, flow cytometry was used to analyze autofluorescence levels in the fibroblasts. These results determined a significant increase in autofluorescencein PD cells after UVA exposure, compared to AMC fibroblasts, thus supporting the electron microscopic observations (FIG. 8H, p<0.001, Unpaired t-test). Moreover, LC3 and p62 expression was investigated after UVA treatment via western blotting. Here an increase in LC3 11 steady state (FIGS. 8J, 8K), as well as p62 (FIGS. 8L, 8M), was seen in PD cells confirming an upregulation of autophagic processing in response to UVA irradiation.

DISCUSSION

The complex and varied nature of PD demands not one, but a 'constellation' of biomarkers with diagnostic and prognostic capacities. In this context, the present invention describes several distinct cellular and molecular alterations in skin fibroblasts obtained from idiopathic PD patients, which mimic core mechanisms characteristically seen in degenerating PD neurons, and may provide a novel platform for preclinical diagnosis and progression biomarkers for PD. The present invention provides robust evidence that sporadic PD fibroblasts can exhibit distinct phenotypic changes, thus suggesting that phenotypes reported in PD afflicted neurons may not be totally cell specific.

Firstly, it was found that the PD fibroblasts exhibited distinct growth and morphology characteristics, not shared by cells originating from apparently healthy individuals. Specifically, the data determine that PD cells divided more rapidly than control cells. The sporadic PD cells were also smaller, more defined, and grew in tightly packed 'school of fish' patterns, thus allowing individual cells to occupy less surface area and providing more room for density-dependent doubling. Additionally, the PD cells were more spindle-shaped, and exhibited reduced contact inhibition (were surrounded by more neighboring cells) that is characteristic of actively dividing fibroblasts. Interestingly, the LRRK2+/+ fibroblasts showed features distinct from sporadic PD (and AMC) cells, in that they grew more slowly and in groups or "bunches," were larger, less defined and less elongated. One factor contributing to these growth and morphology changes in PD fibroblasts could be the increased ROS levels noted in the PD cells. In fact, ROS can affect cellular homeostatic process such as cell proliferation which in turn can also cause cytoskeletal changes. Cytoskeletal destabilization, affecting both the microtubule and actin structure, has been implicated as a major player that paves the way for neurodegeneration in PD.

Secondly, PD fibroblasts showed a greater propensity to accumulate ROS/oxidative stress, and exhibited mitochondrial and autophagic dysfunction. These three interrelated processes, namely oxidative stress, mitochondrial compromise, and autophagic dysregulation, constitute core pathogenic mechanisms in PD. In terms of oxidative stress, it was observed that PD cells displayed higher baseline ROS levels, and greater ROS accumulation upon exposure to UVA, a natural age-related environmental stressor for fibroblasts. Both DCF-DA and Mitosox fluorescence were noted as significantly higher in PD skin fibroblasts compared to AMC cells. This ROS amplification may have contributed to the significantly reduced viability of the PD cells after UVA exposure. Furthermore, the pronounced increase seen specifically in Mitosox fluorescence supported a role for mitochondria-based ROS species in this process.

In this context, mitochondria are key sources of reactive species. Mitochondrial electron transport chain disturbances can allow electrons to be transferred and reduce molecular oxygen to form superoxide and/or hydrogen peroxide. Most importantly, mitochondria play critical roles in regulating cellular energy needs and viability. Therefore, a functional impairment of mitochondria can have a severe impact on cellular homeostasis. The present results showed that PD fibroblasts have lower respiratory control ratio (RCR) relative to AMC cells, which indicates the reduced efficiency of mitochondria to oxidize substrates and produce ATP. Also, the higher proton leak (PL) in PD fibroblasts provides a logical explanation for the reduced RCR since a leaky membrane that leads to proton loss in the OXPHOS circuitry can cause mitochondrial inefficiency. Moreover, the reduced coupling efficiency (CE) in PD cells, relative to the AMC cells, further supports the results demonstrated by RCR and PL. Coupling efficiency is a measure of the fraction of protons used for mitochondrial ATP production proportional to protons leaking through the mitochondrial inner membrane, and hence serves as a supporting parameter for RCR and PL levels. Finally, the structural mitochondrial alterations were found to be consistent with the functional findings. Specifically, the fragmented mitochondrial morphology and reduced fluorescence observed in PD cells (including LRRK2+/+ cells), via rhodamine 123 staining, suggested problems with mitochondrial fission/fusion and in maintaining optimal mitochondrial membrane potential. The ultrastructural findings showing collapsed mitochondria in PD cells also point towards compromised mitochondrial fusion/fission. Furthermore, the ultrastructural data, showing the loss of mitochondrial cristae and mitophagy, also support less than optimal mitochondrial respiration, mitochondrial dysfunction, and reduced mitochondrial viability, in the PD cells.

Some research has revealed that mitochondrial dysfunction is an important feature of degenerating neurons in PD. The present observations, both biochemical and morphological, are interesting in that a 'PD-like' mitochondrial dysfunction is seen in a peripheral non-neuronal cell such as a fibroblast. This suggests that there may be a global mitochondrial defect occurring in PD, which is also expressed outside the nervous system. Damaged mitochondria and oxidative stress may also lead to cytoskeletal destabilization, which maybe a contributor to the growth and morphological changes observed in the PD cells.

Impaired autophagy is as an important process underlying several neurodegenerative diseases, including PD, as evidenced by the collection of toxic, aggregate-prone, intracytosolic proteins in afflicted cells. Auto-activated compensatory mechanism of degradation may explain the increased number of autophagic vacuoles in the brains of PD patients. In support, a similar observation has been found in PD cellular and animal models in which there were more autophagic vacuoles. Nevertheless, this compensatory increase in autophagy may eventually be difficult to sustain, resulting in the build-up of toxic aggregates and neuronal death. The results of the present invention reflecting a widespread appearance of autophagic vacuoles, changes in autophagy proteins, and mitophagy indicate that the PD fibroblasts may rely on such a compensatory mechanism of degradation. Upon a UVA challenge, the PD fibroblasts show a further exaggerated autophagic response, which is unable to counteract the increased accumulation of cellular materials and the loss of cell viability. Interestingly, the observation of this important PD mechanism in a peripheral cell, such as a fibroblast, may be suggestive of a more systemic cellular and molecular impairment in PD that extends beyond neurological compartments, such as in the skin.

CONCLUSION

There is a need in the field for accessible disease- and patient-specific model systems that capture the dynamic aging nature of PD. Specifically, an ideal model system should be reflective of disease status and progression while demonstrating the fundamental features and mechanisms associated with PD neuropathology. The present invention utilizes PD skin fibroblasts as an accessible sample source, which reflects PD molecular changes seen in degenerating dopaminergic neurons, and provides a comprehensive analysis of PD fibroblasts from sporadic PD subjects at multiple levels that identify several specific characteristics that mark PD cells. The data also indicates that basic mechanisms active in neural cells in PD are likely expressed in other non-neuronal cells suggesting a generalized biological defect in PD. The present invention can provide a robust platform for developing peripheral biomarkers of the disease in cells such as fibroblasts, which allow monitoring of disease progression in PD by correlating the clinical phenotype with ongoing cellular and molecular changes.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method of screening and identifying a drug suitable for treating Parkinson's disease (PD), the method comprising:
    a) obtaining a skin fibroblast sample from a subject diagnosed with PD;
    b) growing said skin fibroblast samples in a medium;
    c) generating a PD biomarker profile of said skin fibroblast sample comprising; determining fibroblast growth rate, cell density, cell size and shape, viability, the level of oxidative stress, the level of mitochondria, mitochondrial fragmentation, and/or the level of autophagic vesicles of said skin fibroblast sample;
    d) administering the drug to the PD fibroblast sample and generating a drug-treated PD biomarker profile as in c); and e) comparing the drug-treated PD biomarker profile to the PD biomarker profile
wherein the drug is identified as suitable for treating PD when the comparison of the PD biomarker profile against the drug-treated PD biomarker profile results in the following:
  i) the drug-treated PD skin fibroblasts have a slower growth rate than the PD skin fibroblasts;
  ii) the drug-treated PD skin fibroblasts have a decreased cell density than the PD skin fibroblasts;
  iii) the drug-treated PD skin fibroblasts are larger and less circular than the PD skin fibroblasts;
  iv) the drug-treated PD skin fibroblasts have a lower total reactive oxygen species (ROS) production and a lower mitochondrial ROS than the PD skin fibroblasts;
  v) the drug-treated PD skin fibroblasts have an increase in respiratory control rate (RCR) than the PD skin fibroblasts;
  vi) the drug-treated PD skin fibroblasts have a decreased proton leak than the PD skin fibroblast;
  vii) the drug-treated PD skin fibroblasts have an increase in mitochondria than the PD skin fibroblast;
  viii) the drug-treated PD skin fibroblasts have a decrease in mitochondrial fragmentation than the PD skin fibroblast; or
  ix) the drug-treated PD skin fibroblasts have a decrease in autophagic vesicles than the PD skin fibroblasts.

2. The method of claim 1 further comprising exposing said the PD fibroblast sample in the medium to ultraviolet (UV) radiation for a period of time prior to measuring, wherein said UV induces stress in said fibroblast sample.

3. The method of claim 2, wherein the period of time of UV irradiation ranges from about 3 to 10 days, with about 10 to 30 minutes of exposure per day.

4. A method of screening a subject to identify a suitable drug that treats Parkinson's disease (PD) in the subject, the method comprising:
  a) obtaining a skin fibroblast sample from the subject diagnosed with PD;
  b) obtaining a skin fibroblast sample from an age matched control (AMC);
  c) independently growing said skin fibroblast samples from (a) and (b) in a medium;
  d) generating a PD biomarker profile and AMC reference biomarker profile of said skin fibroblast sample from (a) and (b), respectively, comprising: fibroblast growth rate, cell density, cell size and shape, viability, the level of oxidative stress, the level of mitochondria, mitochondrial fragmentation, and/or the level of autophagic vesicles of said skin fibroblast samples;
  e) administering a drug to the fibroblast sample from the subject and generating a biomarker profile as in step d); and
  f) comparing the drug-treated PD biomarker profile to the AMC biomarker profile;
  wherein the drug is identified as suitable for treating PD in the subject if the drug demonstrates that it revert the PD biomarker profile to the AMC biomarker profile after administration of the drug.

5. The method of claim 4 further comprises exposing said PD fibroblast sample and AMC fibroblast sample in the medium to ultraviolet (UV) radiation for a period of time prior to measuring, wherein said UV induces stress in said fibroblast sample.

6. The method of claim 5, wherein the period of time of UV irradiation ranges from about 3 to 10 days, with about 10 to 30 minutes of exposure per day.

* * * * *